(12) United States Patent
Choi et al.

(10) Patent No.: US 10,384,064 B2
(45) Date of Patent: *Aug. 20, 2019

(54) BIOMIMETIC MULTICHANNEL NEUROSTIMULATION

(71) Applicant: The Research Foundation for the State University of New York, Albany, NY (US)

(72) Inventors: John S. Choi, Brooklyn, NY (US); Joseph T. Francis, Brooklyn, NY (US)

(73) Assignee: The Research Foundation for the State University of New York, Albany ( * ) Notice: Subject to any disclaimer, the term of this patent is extended or adjusted under 35 U.S.C. 154(b) by 0 days.

This patent is subject to a terminal disclaimer.

(21) Appl. No.: 15/984,626

(22) Filed: May 21, 2018

(65) Prior Publication Data
US 2018/0333580 A1 Nov. 22, 2018

Related U.S. Application Data

(63) Continuation of application No. 15/304,305, filed as application No. PCT/US2015/025803 on Apr. 14, 2015, now Pat. No. 9,974,957.
(Continued)

(51) Int. Cl.
*A61N 1/36* (2006.01)
*A61N 1/05* (2006.01)
(Continued)

(52) U.S. Cl.
CPC ........ *A61N 1/36103* (2013.01); *A61B 5/0002* (2013.01); *A61B 5/4064* (2013.01);
(Continued)

(58) Field of Classification Search
None
See application file for complete search history.

(56) References Cited

U.S. PATENT DOCUMENTS 6,463,328 B1 10/2002 John
7,209,788 B2 4/2007 Nicolelis
(Continued)

OTHER PUBLICATIONS

Brockmeier et al., "Subspace matching thalamic microstimulation to tactile evoked potentials in rat somatosensory cortex," 34th Annual International Conference of the IEEE Engineering in Medicine and Biology Society (EMBS), San Diego, CA, pp. 2957-2960 (Aug. 28-Sep. 1, 2012) Aug. 8, 2012.
(Continued)

*Primary Examiner* — Kennedy Schaetzle
(74) *Attorney, Agent, or Firm* — Heslin Rothenberg Farley & Mesiti P.C

(57) ABSTRACT

Sensory information can be delivered to a subject mammal, for example, for restoring a sense of cutaneous touch and limb motion to the subject mammal. A biomimetic electrical signal is generated based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to peripheral touch stimuli and/or peripheral nerve stimulation of the reference mammal. The biomimetic electrical signal is applied to a somatosensory region of a nervous system of the subject mammal to induce an activation response, in a sensory cortex of the subject mammal.

32 Claims, 15 Drawing Sheets

Related U.S. Application Data

(60) Provisional application No. 61/979,425, filed on Apr. 14, 2014.

(51) Int. Cl.
  *A61B 5/00* (2006.01)
  *A61F 2/50* (2006.01)

(52) U.S. Cl.
  CPC ............ *A61B 5/4827* (2013.01); *A61B 5/685* (2013.01); *A61B 5/7267* (2013.01); *A61N 1/0529* (2013.01); *A61N 1/0534* (2013.01); *A61N 1/0551* (2013.01); *A61N 1/36003* (2013.01); *A61N 1/36139* (2013.01); *A61B 2503/40* (2013.01); *A61B 2503/42* (2013.01); *A61B 2562/046* (2013.01); *A61F 2002/5058* (2013.01); *A61F 2002/5061* (2013.01)

(56) References Cited

U.S. PATENT DOCUMENTS

| | | |
|---|---|---|
| 8,112,154 B2 | 2/2012 | Rezai |
| 9,302,103 B1 | 4/2016 | Nirenberg |
| 9,974,957 B2 | 5/2018 | Choi |
| 2005/0096521 A1 | 5/2005 | Anderson |
| 2005/0261601 A1 | 11/2005 | Schuler |
| 2006/0241788 A1 | 10/2006 | Srinivasan |
| 2008/0294579 A1 | 11/2008 | Rapoport |
| 2009/0312817 A1 | 12/2009 | Hogle |
| 2012/0101595 A1 | 4/2012 | Jung |
| 2013/0090706 A1 | 4/2013 | Nudo |
| 2017/0036022 A1 | 2/2017 | Kelly |

OTHER PUBLICATIONS

Heming et al., "Designing a Thalamic Somatosensory Neural Prosthesis: Consistency and Persistence of Percepts Evoked by Electrical Stimulation," IEEE Transactions on Neural Systems and Rehabilitation Engineering, vol. 19, No. 5, pp. 477-482 (Oct. 2011) Oct. 2011.

International Search Report and Written Opinion issued by the U.S. Patent and Trademark Office as International Searching Authority for International Application No. PCT/US2015/025803 dated Dec. 11, 2015 (9 pages) Dec. 11, 2015.

Lenz et al., "Neuronal activity in the region of the thalamic principal sensory nucleus (ventralis caudalis) in patients with pain following amputations," Neuroscience, vol. 86, No. 4, pp. 1065-1081 (Jun. 18, 1998) Jun. 18, 1998.

Stamoulis et al., "Estimation of Brain State Changes Associated with Behavior, Stimulation and Epilepsy," Conf. Proc. IEEE Eng. Med. Biol. Soc., vol. 1, pp. 4719-4722, (2009) 2009.

Daly et al., "Optimal space—time precoding of artificial sensory feedback through mutichannel microstimulation in bi-directional brain-machine interfaces," Journal of Neural Engineering, vol. 9, 13 pages (2012) 2012.

Berg et al., "Behavioral Demonstration of a Somatosensory Neuroprosthesis," IEEE Transactions on Neural Systems and Rehabilitation Engineering, vol. 21, No. 3, pp. 500-507 (2013) 2013.

Tabot et al., "Restoring the sense of touch with a prosthetic hand through a brain interface," PNAS, vol. 110, No. 45, pp. 18279-18284 (2013) 2013.

Corrections to "Tabot et al., "Restoring the sense of touch with a prosthetic hand through a brain interface," PNAS, vol. 110, No. 45, pp. 18279-18284 (2013)," PNAS, vol. 111, No. 2, pp. 875-876 (2014) 2014.

Electrode insertion sites

Array geometries

Pulse train properties

Stimulating configurations bipolar electrode configurations

Time (s)

BIOMIMETIC MULTICHANNEL NEUROSTIMULATION

RELATED APPLICATIONS

This application is a continuation of to U.S. patent application Ser. No. 15/304,305, filed on Oct. 14, 2016, which issued as U.S. Pat. No. 9,974,957 on May 22, 2018, to which this application claims priority, and which was a National Stage Entry of International Patent Application PCT/US2015/025803, which was filed on Apr. 14, 2015, to which this application also claims priority, which claimed priority to U.S. Provisional Patent Application No. 61/979,425, filed on Apr. 14, 2014, to which this application also claims priority, titled BIOMIMETIC MULTICHANNEL NEUROSTIMULATION, the entire contents of which applications are incorporated herein by reference.

GOVERNMENT LICENSE RIGHTS

This invention was made with government support under grant N66001-10-C-2008 awarded by Defense Advanced Research Projects Agency. The Government has certain rights to this invention.

FIELD

The subject technology relates to biomimetic neuro-robotic interfaces for somatosensory prostheses.

BACKGROUND

Somatosensory prostheses relate to an area of research spurred by the development of motor brain machine interface technology. With the advent of these technologies came new possibilities for bidirectional brain machine interfaces for restoring motor and sensory function for patients that have suffered limb loss or spinal cord trauma. One particular set of challenges in the field today is using engineering tools to ensure that the artificial limb will be useable in a wide range of reaching and grasping movements, ideally to the former capacity of the native limb. In this sense, the way in which somatosensory information is encoded into electrical stimulation in the brain becomes very important for enhancing information throughput, discriminability, and naturalness of evoked percepts.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1, Clause 2, or Clause 3. The other clauses can be presented in a similar manner.

Clause 1. A method of delivering sensory information to a subject mammal, the method comprising:
generating a biomimetic electrical signal based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to peripheral touch stimuli and/or peripheral nerve stimulation of the reference mammal; and
applying the biomimetic electrical signal to a somatosensory region of a nervous system of the subject mammal to induce an activation response, in a sensory cortex of the subject mammal.

Clause 2. A system for delivering sensory information to a subject mammal, the system comprising:
a signal generation module configured to generate a biomimetic electrical signal based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to peripheral touch stimuli and/or peripheral nerve stimulation of the reference mammal; and
a signal application module configured to apply the biomimetic electrical signal to a somatosensory region of a nervous system of the subject mammal to induce an activation response, in a sensory cortex of the subject mammal.

Clause 3. A machine-readable medium comprising instructions for delivering sensory information to a subject mammal, the instructions comprising:
generating a biomimetic electrical signal based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to peripheral touch stimuli and/or peripheral nerve stimulation of the reference mammal; and
applying the biomimetic electrical signal to a somatosensory region of a nervous system of the subject mammal to induce an activation response, in a sensory cortex of the subject mammal.

Clause 4: wherein the applying of the biomimetic electrical signal is to a human.

Clause 5: wherein the reference mammal is the subject mammal.

Clause 6: wherein the reference mammal is a mammal other than the subject mammal.

Clause 7: wherein the subject mammal and the reference mammal are of different species.

Clause 8: wherein the biomimetic electrical signal is generated by a prosthetic device.

Clause 9: wherein the sensory cortex of each of the reference mammal and the subject mammal is a primary somatosensory cortex (S1).

Clause 10: wherein the somatosensory region of each of the reference mammal and the subject mammal comprises a primary somatosensory cortex.

Clause 11: wherein the somatosensory region of each of the reference mammal and the subject mammal comprises at least one of a Brodmann area 1, a Brodmann area 2, a Brodmann area 3b, a Brodmann area 3a and a somatosensory thalamic nucleus, such as a Ventral Posterior Lateral (VPL) nucleus of the thalamus, also called the Ventral Caudal (VC) nucleus in humans, or the proprioceptive thalamic region.

Clause 12: wherein the somatosensory region of the nervous system of each of the reference mammal and the subject mammal comprises a thalamic nucleus.

Clause 13: wherein the thalamic nucleus of each of the reference mammal and the subject mammal is a ventral posterior lateral thalamus, also called Ventral Caudal (VC) nucleus in humans.

Clause 14: wherein the peripheral sensory nerve of the subject mammal is in a limb of the subject mammal.

Clause 15: wherein the biomimetic electrical signal is applied to the thalamic nucleus of the subject mammal after the subject mammal has lost at least a portion of the limb.

Clause 16: wherein the natural-response reference signal is acquired from the sensory cortex of the reference mammal in response to a mechanical stimulation of the peripheral sensory nerve of the reference mammal.

Clause 17: wherein the applying of the biomimetic electrical signal is through multiple channels.

Clause 18: wherein the applying is by a microelectrode array.

Clause 19: wherein each of the biomimetic electrical signal, the stimulation reference signal, the stimulated-response signal, and the natural-response signal comprises a spatiotemporal pattern.

Clause 20: wherein each of the stimulated-response signal and the natural-response signal comprises information regarding at least one of local field potentials, spike times/rates, or spike counts.

Clause 21: wherein the biomimetic electrical signal is generated from an algorithm based on the stimulation reference signal, the stimulated-response signal, and the natural-response signal.

Clause 22: wherein the algorithm is derived from a state-space model using the stimulation reference signal, the stimulated-response signal, and the natural-response signal.

Clause 23: wherein the biomimetic electrical signal is generated by a model predictive controller using a state-space model trained from the stimulation reference signal and the stimulated-response signal and optimized using the natural-response signal.

Clause 24: wherein the state-space model comprises a discrete-time linear dynamical model trained from the stimulation reference signal and the stimulated-response signal.

Clause 25: wherein the discrete-time linear dynamical model is defined, at least in part, by equations (1) and (2):

$$x_{t+1} = Ax_t + Bu_t + \epsilon_x \quad (1)$$

$$y_t = Cx_t + \epsilon_y \quad (2)$$

wherein each vector containing stimulation channel magnitudes at time t is denoted $u(t) \in \mathbb{R}^m$, the state is denoted by $x \in \mathbb{R}^n$, and the output is denoted $y \in \mathbb{R}^p$. $\epsilon_x \sim N(0, Q)$ and $\epsilon_y \sim N(0, R)$.

Clause 26: wherein A, B, C, Q, and R are determined using system identification techniques including, but not limited to, subspace identification, least-squares regression with filter bank (Laguerre, Gamma) features as inputs followed by a model reduction technique such as Balanced Truncation. A, B, and C could also represent local linearizations of a nonlinear model which include, but are not limited to, neural networks, Volterra series models, and kernel regression methods.

Clause 27: wherein the model predictive controller minimizes a squared Euclidean distance between y(t) and a target output signal.

Clause 28: wherein the model predictive controller operates to:

minimize $z^THz + \kappa\phi(z)$ subject to $Tz = 0$ wherein $\kappa$ is a weighting parameter to prioritize the contribution of the log barrier, z is formed by stacking the states $x_t$, $u_t$ for t=1, 2, . . . length of the control horizon. H represents quadratic penalties imposed by taking Euclidean distances between the output and a desired response signal for each time point. T is the matrix representing the relationships between adjacent time points as in Eqn. (1).

Clause 29: wherein:

minimize $z^THz + \kappa\phi(z)$ subject to $Tz = 0$ is solved using convex optimization.

Clause 30: wherein the biomimetic electrical signal is generated by the model predictive controller, optimizing using an average of a plurality of natural-response signals as target waveforms.

Clause 31: wherein the biomimetic electrical signal is generated by the model predictive controller, optimizing using a target generated from a predictive neural encoding model of a plurality of natural-response signals.

Clause 32: wherein the model predictive controller employs convex optimization.

Clause 33: wherein the model predictive controller minimizes mean-square error.

Clause 34: wherein the activation response comprises a signal emanating from the sensory cortex of the subject mammal

BRIEF DESCRIPTION OF THE DRAWINGS

FIG. 4A shows trial-average tactor angular position (negative is towards the skin). The shaded portion of the top plot corresponds to the period of time when the actuator was in contact with the skin. FIG. 4B shows average multichannel LFP response to natural touch, each curve representing an S1 recording channel. Channels are sorted according to their overal response amplitude for this touch site. FIG. 4C shows optimized microstimulation, each curve represents a distinct stimulation channel. FIG. 4D shows average microstimulation LFP response.

FIG. 6A shows in the left cartoons, the size of each square represents the response magnitude, while the shade of each square represents the virtual touch reproduction accuracy. The * symbols indicate touch sites in which virtual touch outperformed the condition-shuffled natural surrogate ($p_{mimic}<0.1$, one-tailed sign test, Bonferroni correction over 54 touch conditions). * indicates touch conditions in which the resulting single-trial accuracy was significantly better than that of condition-shuffled natural responses ($p<0.1$, one-tailed sign test, Bonferroni correction over 54 touch conditions). FIG. 6B shows increased single trial accuracy corresponds to touch sites with larger magnitude of evoked LFP.

FIG. 7A shows decoding rates when only considering trials that were of short (150 ms) duration and were light, medium, or strong. FIG. 7B shows classification rate for decoding duration and touch site when the touch strength is known. FIG. 7C shows classification rate for all trials in the first column. The second column shows the accuracy in decoding amplitude and duration when the touch site is known.

FIG. 9A shows spatial correlation of electrode usage under optimized ITMS and multi-unit activity (MUA) during natural touch. Each dot within an inset represents an (electrode, touch site) pair, and the insets correspond with different touch patterns of varying duration and amplitude. FIG. 9B shows the top row shows the post-onset MUA responses in VPL during natural touch and the corresponding optimized ITMS. Each trace represents the unit-average probability of spiking, with 2 ms bins, for a particular touch site. The two columns correspond with two different touch durations of 150 ms and 250 ms. The optimized ITMS waveforms in the bottom row are the maximum currents used by any input channel for each time point. The temporal characteristics of the ITMS resemble that of the natural spiking activity.

DETAILED DESCRIPTION

Figure 1A:
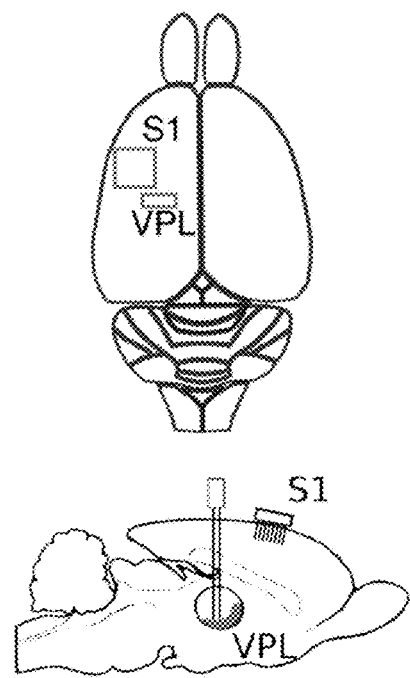
FIG. 1A shows insertion sites for the S1 and VPL electrode arrays.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Some aspects of the subject technology relate to somatosensory prosthetic devices for restoring the sense of cutaneous touch and limb motion to patients who have suffered limb loss or spinal trauma. Some embodiments of the subject technology can be used for encoding touch information measured by sensors on advanced robotic limbs, into patterns of electrical pulses through electrode arrays targeted to the patient's intact brain areas that represent somatosensation. Electrical stimulation, applied naively, is a rather crude method of evoking neural responses, and its effectiveness for use in sensory prosthetics depends at least in part on the extent to which the stimulation pulse patterns "speak the same language" as the neural system it is influencing. In some embodiments, the subject technology uses optimization techniques to automatically learn the best way to stimulate the brain such that the evoked effects, i.e., the understanding, is desirably, but not necessarily, as similar as possible to the former neural responses to sensations on the native limb. Some aspects of the subject technology use computational modeling and numerical optimization.

In some embodiments, the subject technology can provide a solution for rapidly developing encoding algorithms for sensory neural prosthetic devices. In contrast to techniques for encoding somatosensory information into electrical stimulation pulses that rely on painstaking manual calibration of a potentially very large number of parameters, some embodiments of the subject technology provide for automatic calibration of many parameters in animal subjects prior to implementation in humans. In some aspects of the subject technology, the automatic calibration involves modeling the fine-grained spatiotemporal responses evoked by microstimulation out of a multichannel array and then subsequently controlling the stimulation so as to evoke responses as close as possible to native responses. This bypasses the calibrations of many microscopic parameters, since they would be automatically optimized based on neural responses, which are potentially far more informative than verbal or psychophysical reports.

Some aspects of the subject technology relate to generation of encoding algorithms for animal subjects implanted with electrode arrays for stimulation and response recording. The resulting encoding algorithms can be applied to or generalized onto human subjects, perhaps with a different set of arrays.

Some aspects of the subject technology relate to bidirectional brain machine interfaces for restoring motor and sensory function for patients that have suffered limb loss or spinal cord trauma, e.g., in somatosensory prostheses providing motor brain machine interface. Some embodiments combine somatosensory prostheses with artificial limbs and provide biomimetic neuro-robotic interfaces. Some aspects of the subject technology can be applied to use of artificial limbs in a wide range of reaching and grasping movements, ideally, but not necessarily, to the former capacity of the native limb. In this sense, the way in which somatosensory information is encoded into electrical stimulation in the brain becomes very important for enhancing information throughput, discriminability, and naturalness of evoked percepts. Some aspects of the subject technology facilitate the development and/or implementation of encoding algorithms to achieve these goals.

Lost sensations, such as touch, may be restored by electrical stimulation along the sensory neural pathways. Used in conjunction with next-generation prosthetic limbs, this stimulation could artificially provide cutaneous and proprioceptive feedback to the user. Microstimulation of somatosensory brain regions can produce modality and place-specific percepts, and several stimulus parameter variations can be discriminable. Prior to the subject technology, systematic methods for encoding external stimuli into patterned, biomimetic multi-channel microstimulation were lacking. Particularly, generating spatiotemporal patterns for explicitly evoking naturalistic neural activation had not been explored. In some aspects of the subject technology, the problem of building a sensory neural prosthesis is addressed by modeling the dynamical input-output relationship between multichannel microstimulation and neural responses, and then optimizing the input pattern for evoking naturally occuring touch responses as closely as possible. In an example, we focused on the hand regions of VPL thalamus and S1 cortex of anesthetized rats and produced, by the subject technology, responses that are highly similar to their natural counterparts. The patterns also evoked responses that preserved most of the information of physical touch parameters such as amplitude and stimulus location. In some embodiments, the subject technology can restore naturalistic levels of information transfer for an afferent neuroprosthetic.

In some embodiments, the subject technology can be applied to treatment of loss of somatosensation by direct electrical stimulation of the central nervous system. Assessment of the naturalness of microstimulation-induced sensations is difficult in animal models, since it has been largely achieved by training animals to report these sensations as being conceptually "higher" or "lower" in some regard compared to natural stimuli. For example, it has been demonstrated that macaques could judge whether microstimulation trains felt more intense than a natural skin indentation. The subjects could similarly report spatial comparisons (i.e., "more medial than") as well. Sensitivities to variations of microstimulation temporal pattern, spatial variation, and level of randomness have been explored. However, it is unlikely that the simple heuristically chosen pulse patterns, often involving only a single electrode at a time, used in these studies are sufficient to recreate natural cortical activation and natural sensations. Indeed, in humans, constant-amplitude pulse trains applied to single electrodes in the ventral caudal (Vc) thalamus have been shown to evoke percepts that are "unnatural" feeling. As stimulation patterns increase in complexity, e.g., by increasing the number of channels, the difficulty of assessing performance psychophysically in animals increases, perhaps prohibitively.

In some aspects of the subject technology, the realism of microstimulation-induced sensations is increased using dynamic, biomimetic encoding algorithms that are specifically tuned to the neuronal circuit at hand. A relatively simple method of biomimetic encoding is to, on every electrode, inject current pulses according to the predicted naturally occurring firing rate. Some aspects of the subject technology involve the recognition that systems and methods of biomimetic encoding should not be based on an assumption that a one-to-one correspondence between a stimulation pulse and elicited spike exists. Electrophysiological evidence suggests that each pulse instead produces a spatiotemporal blur of activity involving many cells. Indeed, for the range of currents likely to be useful for evoking percepts, a single microelectrode can have direct effects on neuronal elements within a surrounding distance, e.g., 50-100 µm of their conducting areas.

In some embodiments of the subject technology, microstimulation pulse patterns are delivered at locations upstream of the target population in a manner that trans-synaptically induces desired downstream activation. To this end, some aspects of the subject technology employ a model-based control method capable of eliciting naturalistic responses in the somatosensory cortex via optimized patterns of intra-thalamic microstimulation (ITMS). In some embodiments, the ITMS patterns spatiotemporally resemble naturalistic spike rates, and their evoked responses preserve most of the information of touch parameters.

In some embodiments, an activation response to a stimulation of a peripheral sensory nerve of a subject (e.g., patient) resembles or imitates a natural neural activation response to a stimulation of a peripheral sensory nerve of the subject. In some embodiments, an activation response induced by application of a biomimetic electrical signal can include one or more of a variety of detectable events. An activation response can include a signal or related activity in a sensory cortex or other region of the subject. Signals induced in the subject can be detected by a microelectrode array at or near a region of its generation. Alternatively or in combination, signals induced in the subject can be detected by electroencephalography (EEG) on a surface of the subject (i.e., by surface EEG). An activation response can include a motor activity of the subject. For example, an activation response can include a reflexive act (e.g., movement of a limb from a rest position, etc.) induced by application of the biomimetic electrical signal. An activation response can include a voluntary indication by the subject. For example, the subject can express (i.e., verbally, by gesture, by input to a device, etc.) an indication of one or more perceived sensations that is induced by application of the biomimetic electrical signal. The subject can provide the indication as a description, a selection of one of a plurality of available responses, etc. The indication can include information regarding time of onset, time of termination, duration, frequency, intensity, and/or quality of the perceived sensation.

Examples

In our in-vivo study, two separate microelectrode arrays (See FIGS. 1a and 1b) performed recording and stimulation synchronously. The first, situated in the forelimb representation of the VPL thalamus, delivered the microstimulation, and the second, situated in the corresponding projection area in S1, measured ongoing field potentials during stimuli (natural touch or microstimulation). Inputs can be provided by electrical stimulation or other means, such as optogenetic stimulation or any method that induces neural activity.

Figure 2:
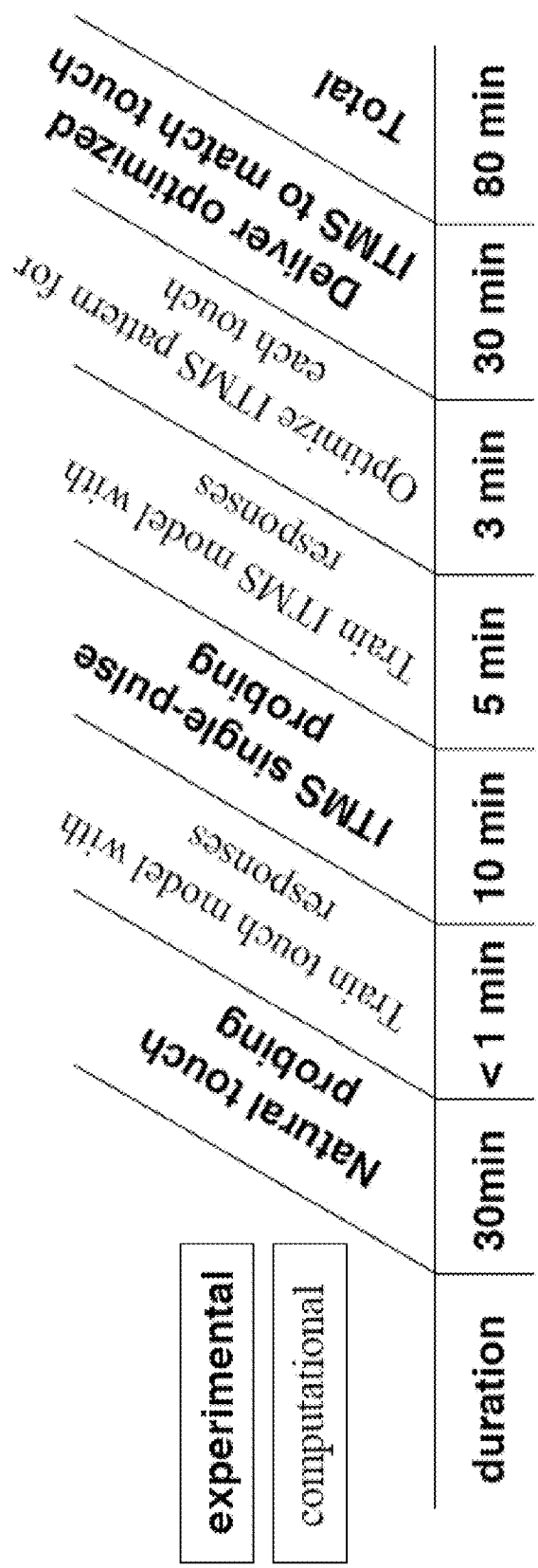
FIG. 2 shows an experimental timeline for Intra-thalamic microstimulation (ITMS).
Figure 3A:
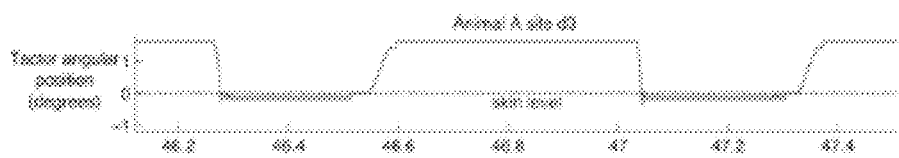
FIG. 3A shows tactor angular position as a function of time for a sample of data (negative is towards the skin). The shaded portion of the curve represents periods of time in which the tactor was in contact with the skin.
Figure 3B:
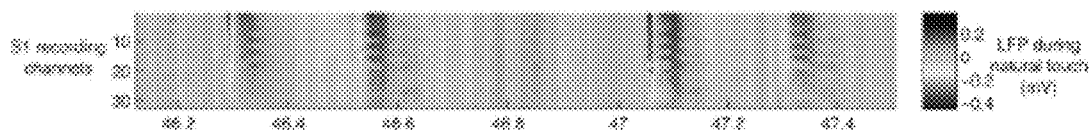
FIG. 3B shows Multichannel S1 LFP for 32 channels during natural taction. Channels are sorted by their overall response amplitude for this touch site.
Figure 3C:
FIG. 3C shows Optimized microstimulation delivered through 8 channels. The shade indicates the amplitude of current, and channels are shown sorted by their overall usage for this touch site.
Figure 3D:
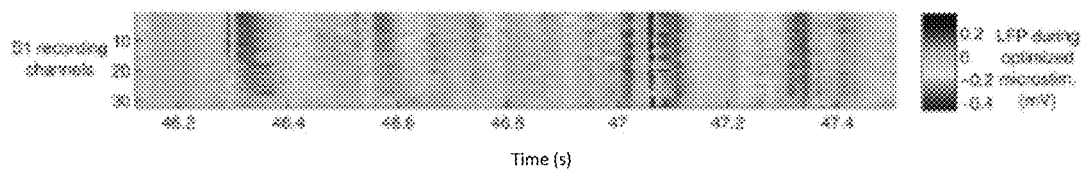
FIG. 3D shows S1 LFP during optimized microstimulation.
Figure 3E:
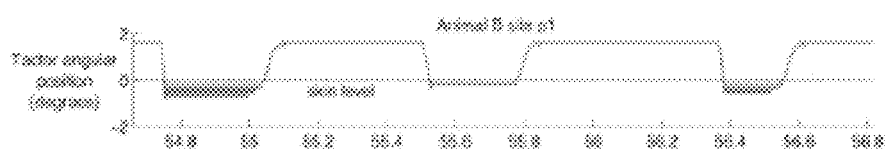
FIG. 3E, FIG. 3F, FIG. 3G, and FIG. 3H show similar plots for a different dataset.
Figure 3F:
Figure 3G:
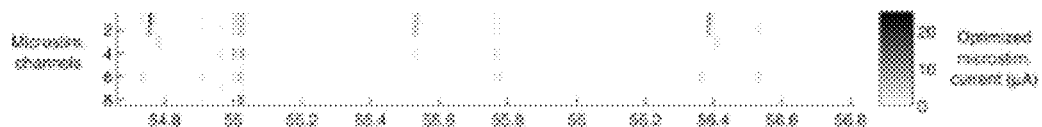
Figure 3H:
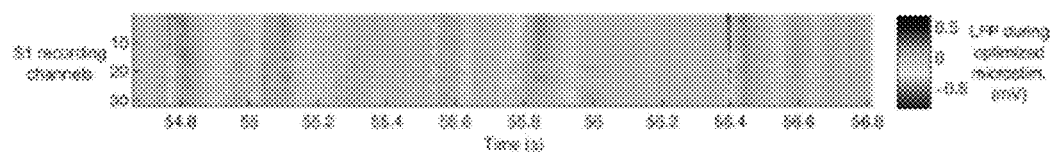
Figure 4A:
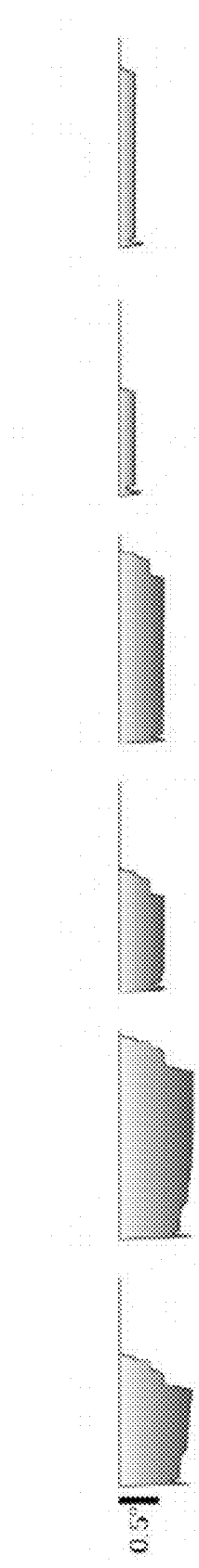
FIG. 4A, FIG. 4B, FIG. 4C, and FIG. 4D show post-touch-onset trace of the trial-average LFP for 6 touch patterns on a single touch site.
Figure 4B:
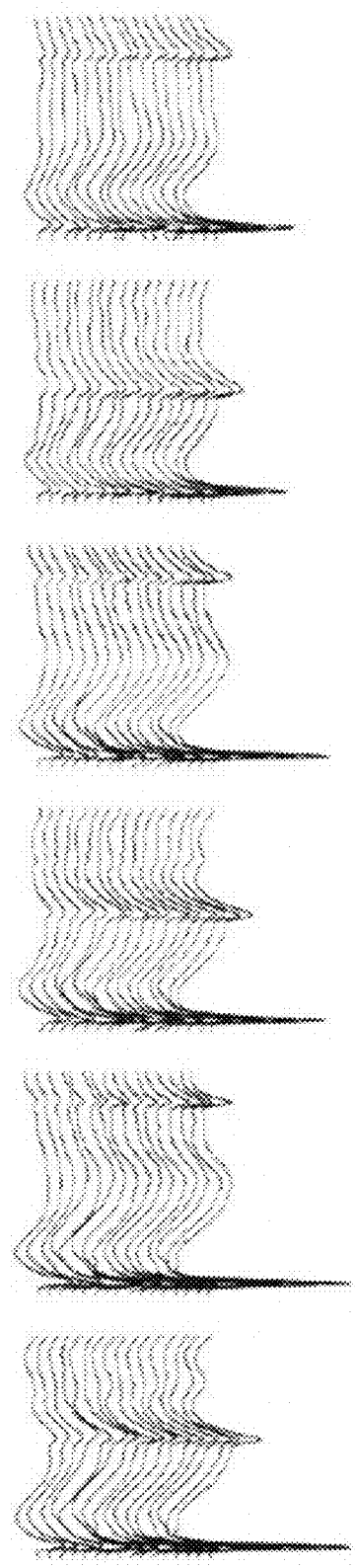
Figure 4C:
Figure 4D:
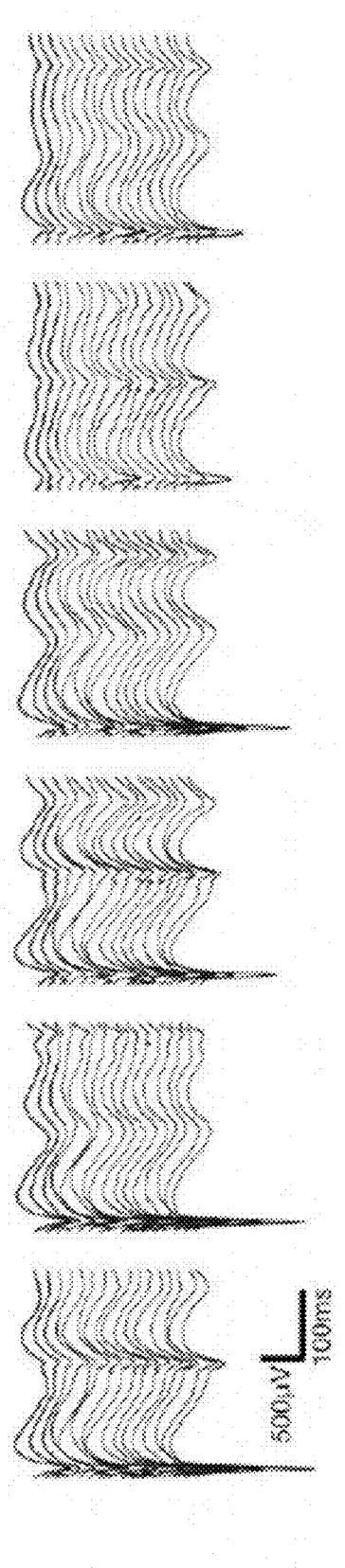

We performed the following procedure in rats (See FIG. 2). A set of natural downstream responses are obtained to serve as templates. A linear dynamical model of responses is learned from probing microstimulation data. A controller then optimizes a set of pulse patterns that, in terms of the model, approximates the natural downstream responses as closely as possible. The set of optimal patterns is then applied to the input brain region, the responses are recorded, and the similarity of the responses assessed. Herein, we consider multielectrode recordings of the local field potentials (LFP). As an alternative, sets of spike trains or spike counts can be used, but as a continuous signal the LFP is simpler for state-space modeling. In addition, we can use mean-square error and correlation as metrics amenable to highly efficient convex optimization. This study concentrates on characterizing the neural responses to both natural taction and optimized microstimulation along with their similarity.

Surgical Methods

Figure 1B:
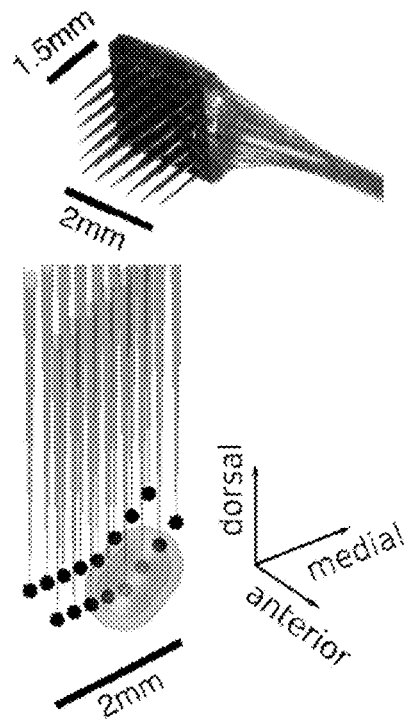
FIG. 1B shows dimensions of S1 array (top) and VPL array (bottom).

Four female Long-Evans rats (250-350 g) were implanted with electrode arrays in VPL and S1 (See FIG. 1b). The array in VPL (MicroProbes Inc.) was a 2×8 grid of 70% platinum 30% iridium 75 µm diameter microelectrodes, with 500 µm between the rows, and 250 µm inter-electrode spacing within the rows. The microelectrodes had a 25:1 taper on the distal 5 mm with a tip diameter of 3 µm. The approximate geometric surface area of the conducting tips was 1250 µm². The shank lengths were custom designed to fit the contour of the rat VPL. Both rows were identical and the shaft lengths for each row, from medial to lateral, were (8, 8, 8, 8, 8, 7.8, 7.6, 7.4) mm.

The cortical electrode array (Blackrock Microsystems) was a 32 channel Utah array (See FIG. 1b). The electrodes are arranged in a 6×6 grid excluding the 4 corners, and each electrode is 1.5 mm long. A single craniotomy that exposed the cortical insertions sites for both arrays was made, and after several probing insertions with a single microelectrode (FHC) in an area 1 mm surrounding the stereotaxic coordinates for the digit region of S1 (4.0 mm lateral and 0.5 mm anterior to bregma), the Utah array was inserted using a pneumatic piston.

The VPL electrode array was centered on stereotaxic coordinates for the hand representation in the medial subdivision of VPL: 2.8 mm lateral, 2.4 mm posterior to bregma. Vertical insertion of the electrodes was made to a depth of 6-7 mm. Spiking units with hand-specific receptive fields were identified by audio recordings, and fine changes to the electrode depth were made to maximize the number of responsive units observed across the array.

Recording LFP During Natural Touch Probing

Multichannel local field potentials were collected during tactile stimulation with a neural signal acquisition system (RZ2, Tucker-Davis Technologies). After insertion of electrode arrays in the hand region of VPL and its analog in S1 (see FIGS. 1a and 1b), physical touch stimulation was administered to 3-9 sites on the ventral surface of the right forepaw with a precision tactor. In some examples, the recording can be via any method that records information from a neural ensemble, including electroencephalography (EEG), magnetoencephalography (MEG), and functional magnetic resonance imaging (fMRI).

The touch patterns consisted of a touch-hold-release sequence parameterized by a pressure and duration. For each site, 3 different pressures and 2 different touch durations were applied. A shuffled series of 25 instances of each of the 6 patterns were presented with random time intervals in between the touches.

A plastic bar 9 cm in length affixed to a DC servomotor (Maxon RE-25) fitted with an optical encoder (Maxon HEDS-55) applied the tactile stimulation. Timing of contact and level of skin indentation were controlled via the motor's angle, which was accomplished by a proportional derivative (PD) controller implemented on a DSP onboard the neural recording system. The amplitude of the force applied by the bar is directly proportional to the skin indentation by Hooke's Law. For the purposes of this work, however, we present results in terms of the lever angle in degrees.

The post-event LFP responses for each (touch site, pattern) combination were collected up to 300 ms following touch onset. These responses were used as target waveforms for optimizing the multi-channel intrathalamic microstimulation (ITMS). Some example waveforms and a channel map capturing the spatial extent of excitation are shown in FIGS. 4 and 5.

Recording and Modeling LFP Response to Probing Microstimulation

Figure 1C:
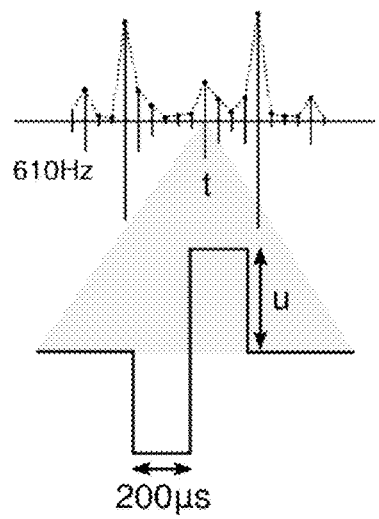
FIG. 1C shows temporal representation of pulse trains. For each a channel a constant frequency pulse train consisting; of symmetric biphasic pulses is amplitude-modulated by an envelope that is designed or optimized.
Figure 1D:
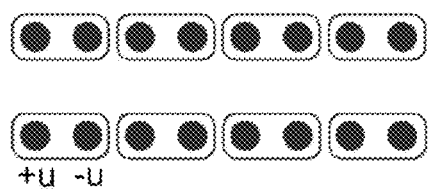
FIG. 1D shows the input channels in this work consisted of adjacent bipolar pairs of electrodes. For 16 channels, this resulted in 8 independent inputs.

To train a model of the cortical LFP response to VPL microstimulation input, we used a probing sequence consisting of randomly timed microstimulation pulses. A multichannel microstimulator (IZ2, Tucker-Davis Technologies) delivered the pulses to 8 non-overlapping bipolar configurations spanning the VPL electrode array (See FIGS. 1c and 1d for illustration). We used bipolar configurations since they produced less stimulation artifact in cortical recording channels than monopolar ones. Pulses were symmetric and biphasic (200 us per phase). Symmetric pulses were chosen because of their relative safety compared to asymmetric pulses. The choice of pulse width was chosen on the basis of consistency with similar studies. Three different stimulation amplitudes {10, 20, 30} µA were used in the probing phase of our work. From the set of amplitude/configuration pairs, a random sequence of microstimulation pulses were drawn and delivered as a marked Poisson process with a mean frequency of 5 Hz. The resulting probing sequence lasted ~8 minutes, and each unique combination of configuration/amplitude was repeated 50-120 times.

A discrete-time linear dynamical model was trained using the microstimulation probing data: an 8 dimensional input for the microstimulation and a 32 dimensional output for the S1 LFP responses. A state dimensionality of 50 was chosen empirically as a tradeoff between model complexity and prediction accuracy.

$$x_{t+1} = Ax_t + Bu_t + \epsilon_x \quad (1)$$

$$y_t = Cx_t + \epsilon_y \quad (2)$$

Each vector containing the stimulation channel magnitudes at time t is denoted $u(t) \in \mathbb{R}^m$, the state is denoted by $x \in \mathbb{R}^n$, and the output is denoted $y \in \mathbb{R}^p$. $\epsilon_x \sim N(0, Q)$ and $\epsilon_y \sim N(0, R)$. The system parameters (A, B, C, Q, R) were learned using a subspace method (See algorithm 4.8 in (Van Overschee and De Moor, 2011) for details). Subspace system indentification methods estimate a low dimensional state sequence $x_1, x_2, \ldots$ and corresponding system matrices based on linear combinations of input and output data. All subspace methods involve, as an intermediate step, choosing the n most meaningful state dimensions based on a singular value decomposition of transformed data matrices.

Optimizing Microstimulation Patterns

Using a model predictive controller, we optimized patterns of microstimulation pulses in order to imitate the natural touch responses for each unique touch type attempted during probing. A model predictive controller yields an optimal input sequence that drives the linear model through a desired response—in our case the trial-average of the LFP responses for each force pattern and touch site location. Although a predictive neural encoding model could have been used, we used the trial average in this study for simplicity.

On each stimulation channel (bipolar pair of electrodes), the optimized input signal corresponds to a time-varying amplitude envelope of a constant-frequency pulse train (610 Hz in our study, roughly twice the upper cutoff frequency of the LFP filter). The modulated pulse train consisted of negative-first biphasic pulses. We emphasize that only the non-negative amplitude of the pulse train is optimized, and hence the pulses remain at a single polarity. Changing the polarity switches the order in which current is sinked or sourced on each of the two adjacent electrodes, and response to negative polarities are not linearly related to the response to positive polarities.

We assume that at time t, a desired neural trajectory $y^d$ for the times $t+1, \ldots, t+T-1$ is available. The horizon T governs the amount of future time that the controller considers in optimizing control inputs. In practical (causal) applications, this desired signal could be the output of a predictive response model that, using sensor information available up to t, outputs a predicted neural response for T−1 future time points. Alternatively, $y^d$ could also be a precomputed/recorded neural trajectory. For this study, we treated $y^d$ as completely known, i.e., we set it to the peristimulus trial average of the natural response for each touch condition.

The primary goal of the controller is to minimize the squared Euclidean distance between y(t), the system output under the applied input sequence, and the desired output signal: $\Sigma_{\tau=1}^{T} \|y^d(t+\tau)-y(t+\tau)\|^2$. The optimization is done over a horizon of T steps. It is common in MPC implementations for the first dt time steps of inputs to be applied to the system, and the new states observed. The optimization is then repeated starting from the new state and time step. In this study, however, we trivially chose T to be approximately the full length of the touch response (touch duration+100 ms).

As in the modeling step, the pulse sequence consisted of a 610 Hz train for each stimulating channel, with the amplitude of each pulse modulated by a discrete-time signal u(t). The stage cost l shown in Eqn. 4 consists of the sum of squared output errors between $\hat{y}(t)=Cx(t)$ and a desired output, $y^d(t)$ across a horizon of T time steps. At each time step from $\tau=t, \ldots, t+T$, the controller incurs a cost of $l_t(x(\tau), u(\tau))$. The stage cost, $l_t$, represents the tracking error magnitude encountered at time t. The model dynamics are enforced by equality constraints relating $x(\tau)$, $u(\tau)$, and $x(\tau+1)$. The system evolution in this case is deterministic and the optimization does not depend on the density of $\in_x$ or $\in_y$ in Eqn. 1.

We imposed range constraints on the inputs $u(\tau)$. As we mentioned before, the stimulation signal is intentionally restricted to have nonnegative current values, since it represents only the amplitudes of biphasic pulses, and not their polarities. Using a bound constraint on $u(\tau)$, we set the maximum allowed current to $I_{max}=25$ µA.

$$\text{minimize} \sum_{\tau=t}^{t+T} l(t, x(\tau), v(\tau))$$

$$\text{subject to } 0 \leq u(\tau) \leq I_{max}, \tau = t, \cdots, t+T-1 \quad (3)$$
$$x(\tau+1) = Ax(\tau) + Bu(\tau)$$
$$v(\tau+1) = (1-\alpha)v(\tau) + \alpha \sum_i u_i(\tau)$$

$$l(t, x(\tau), v(\tau)) = \|y^d(t) - Cx(\tau)\|^2 + \mu \|v(\tau)\|^2 \quad (4)$$

The stage cost l is time-varying since it must penalize deviation from the desired trajectory $y^d$.

Although the primary objective of the stage cost l to penalize deviation from a desired trajectory $y^d$, it also includes a term that penalizes the absolute value of a low-pass filtered version of the summed inputs, denoted $v(\tau)$. This has the effect of economizing on current injection across the stimulating array and across time. We noticed that without this penalty, some of the less effectual inputs would be driven to continuously stimulate at significant amplitudes. Although these inputs would be accomplishing nominally better output tracking over the control horizons, they were stimulating at significant supra-threshold amplitudes without much pertinent effect on the measured field potentials. We suspect that these were either channels that influenced a part of S1 that was only partially picked up by our recording array. The rationale behind penalizing a low-pass filtered version of the inputs rather than the instantaneous input was to preferentially reduce long trains.

The low-pass filter contained a single pole at (1−α), which corresponds to a time constant $\tau_{lp}$ by Eqn. 5. This time constant was set to 100 ms.

$$\alpha = \frac{1}{\tau_{lp} F_s + 1} \text{ where } F_s \text{ is the sampling frequency} \quad (5)$$

This method of penalizing a filtered version of the inputs is very similar to the method used by Ahmadian et al. (2011). In that work, however, the optimization was done over raw current waveforms, and the penalty on slow current injection served primarily the purpose of limiting charge build-up, which is well known for causing electrode corrosion or tissue damage near contacts. In our work, charge balance is immediately restored with each biphasic pulse, since our optimization is on the amplitude envelope of a stereotyped pulse train, and so the penalty on v is primarily meant to encourage current efficiency of solutions.

An augmented state vector $\tilde{x}(t)=(x(t), 1, v(t))$ is formed so that the cost $\|Cx(t)-y^d(t)\|^2$ can be written as a quadratic expression of $\tilde{x}(t)$, i.e., $\tilde{x}(t)^T Q(t) \tilde{x}(t)$ where the Hessian Q encodes the Euclidean distance between Cx and $y^d$ as a function of $\tilde{x}$.

$$Q(t) = \begin{bmatrix} E(t)^T E(t) & 0 \\ 0 & \mu \end{bmatrix}, E(t) = [C \quad -y^d(t)] \quad (6)$$

The objective in Eqn. 3 can be put into a quadratic form by stacking the augmented state and input variables for each time in the horizon, i.e. $z=(u(t), \tilde{x}(t+1), u(t+1), \ldots, u(t+T-1), \tilde{x}(t+T))$. The objective is the quadratic function $z^T H z$ where H is the Hessian of the overall cost with respect to z. Since the immediate cost at time t is only a function of $\tilde{x}(t)$, this matrix is block diagonal, with $Q(t+\tau)$ $\tau=1, \ldots, T$ occupying blocks corresponding to $\tilde{x}(t+\tau)$). The equality constraints can similarly be put into a matrix function $Tz=0$ where T is block-tridiagonal. The blocks encode appropriately the linear dependence of $\tilde{x}(t)$ on $\tilde{x}(t-1)$ and $u(t-1)$.

For implementing the bound constraints on the input, a log barrier $(z) = \Sigma_{t=0}^{T-1} \Sigma_{i=1}^{m} -\log(u_i(t)) - \log(I_{max} - u_i(t))$ was appended to the cost. The Eqn. 3 then can be written in a simplified form as:

minimize $z^T H z + \kappa \phi(z)$ subject to $Tz=0$ (7)

where κ is a weighting parameter to prioritize the contribution of the log barrier. The solution can be computed efficiently using convex optimization techniques. We used an infeasible-start Newton method in which a step δz such that z+δz satisfies a linear approximation to the Karush-Kuhn-Tucker (KKT) conditions of optimality. The conditions are that the gradient of the Lagrangian of Eqn. 7 vanishes and z is feasible, i.e. $\nabla_z L(z, v)=0$ (where $L=z^T H z + \kappa \phi(z) + v^T T z$) and $Tz=0$. These conditions, when linearized, produce a system of linear equations that can be solved efficiently by the methods used in (Wang and Boyd, 2010). It can be shown that a dense system of equations of this size requires $O(T^3(n+m)^3)$ computation. However, the block tridiagonal structure of T and the block diagonal structure of H can be exploited since solution of block tridiagonal systems can be done in $O(T(n+m)^3)$ time.

Initially, MPC was run for each touch condition (site, amplitude, duration) offline. The desired trajectory in each case was the trial-averaged natural touch response with τ=0 corresponding to touch onset and T=hold duration+50 ms. The microstimulation pattern begins at touch onset and continues up until T. A possible design choice could have been to optimize the stimulation starting slightly before touch onset. This could lead to better control accuracy as the system can be "prestimulated", but it would require a corresponding delay to retain causality. In reality, the physiological latency from touch onset to cortical response (9 ms) and the latency to ITMS (2 ms) leads to a window of 7 ms during which the system could be "prestimulated." However, prestimulation did not occur consistently nor with significant effect.

Once found, the optimized ITMS patterns were applied through the VPL array. The patterns for each touch type were applied in the same order and timing as the original natural touch stimuli for each forepaw location. We define the term virtual touch to refer to stimulating with optimized patterns of microstimulation corresponding to a particular type of natural touch.

TABLE 1

Table of linear model performance for modeling the cortical responses to probing microstimulation.
+/−1 standard deviation across folds during 4-fold cross-validation.

| Animal | Variance accounted for (%) | Correlation coefficient |
|---|---|---|
| A | 51.3 ± 5.7 | 0.718 ± 0.036 |
| B | 17.6 ± 0.7 | 0.421 ± 0.008 |
| C | 26.2 ± 6.5 | 0.519 ± 0.061 |
| D | 7.6 ± 2.8 | 0.29 ± 0.028 |

Results

LFP Response Model Goodness-of-Fit

The cortical LFP response to microstimulation was modeled with the linear state-space model described in the previous section. Across rats, the model on average accounted for 25.67%±18.7 of the variance in the time periods that were within 400 ms after a stimulation pulse. The correlation coefficient over the same time windows varied from 0.29 to 0.718 (average of 0.487) across rats. Table 1 shows the model performance under 4-fold cross-validation on the ITMS probing data.

Accuracy in Reproducing Natural Responses

The optimized ITMS waveforms elicited neural responses that were spatiotemporally similar to their natural counterparts across touch sites and patterns. Across all conditions and rats, the correlation coefficient between the average natural and virtual responses was 0.775±0.05. If the comparison was made only for periods of time that were within 100 ms of touch onset, the correlation coefficient was 0.90±0.03. FIG. 3 shows two segments of tactor position, natural LFP responses, optimized microstimulation, and the LFP responses to virtual touch.

Examples of the average temporal responses to different touch patterns are shown in FIG. 4. Natural touch elicits a strong, brief potential 9-15 ms after touch onset, followed by a recovery period lasting 150-200 ms. Another temporal feature is the smaller negative potential that occurs shortly after touch-offset when the actuator starts rising away from the touch site. The corresponding optimized microstimulation pattern is shown in FIG. 4c. FIG. 4d shows the resulting average LFP response.

Figure 5C:
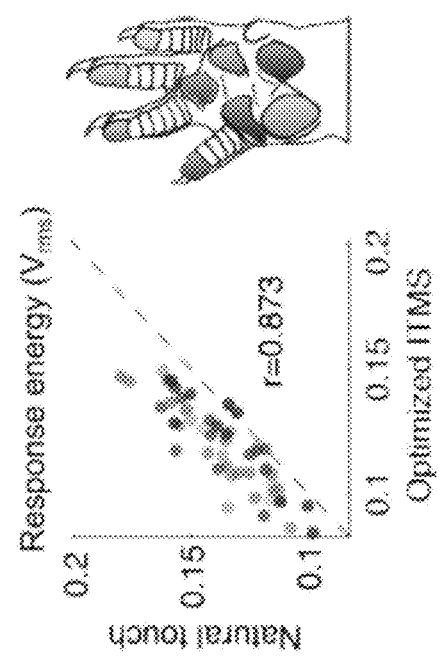
FIG. 5C shows a comparison between the modeled reproduction accuracy (correlation coefficient) of optimized ITMS and the actual accuracy obtained in-vivo. Each point corresponds with a touch condition, and the touch site is color coded according to the touch site (see inset).
Figure 5D:
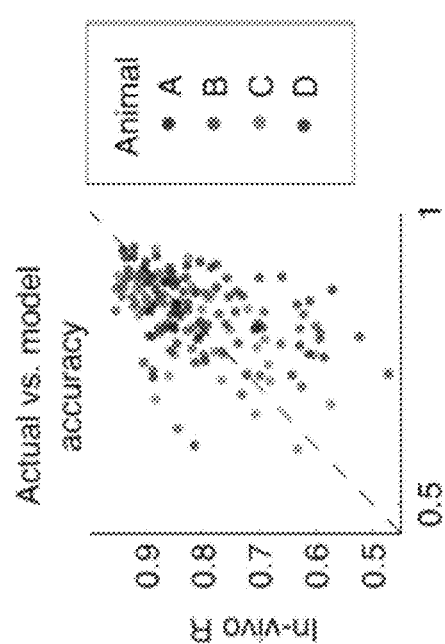
FIG. 5D shows a channel-average amplitude comparison for natural touch and optimized ITMS in-vivo. Each point represents a unique touch site/pattern combination.
Figure 5A:
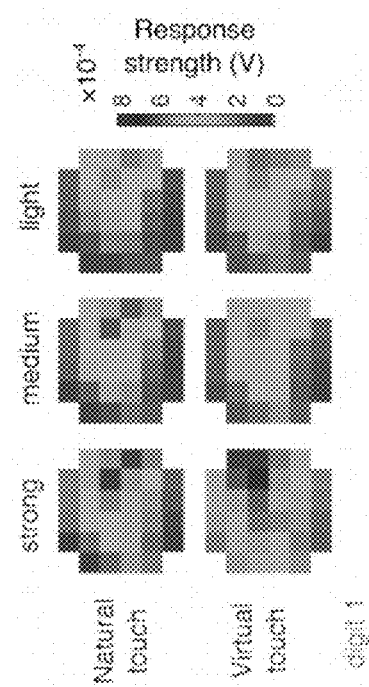
FIG. 5A and FIG. 5B show spatial response topologies natural and virtual touch. Each pixel corresponds with a recording electrode, and the color indicates the LFP strength, which we define as the most negative voltage in the response window (0-300 ms).
Figure 5B:
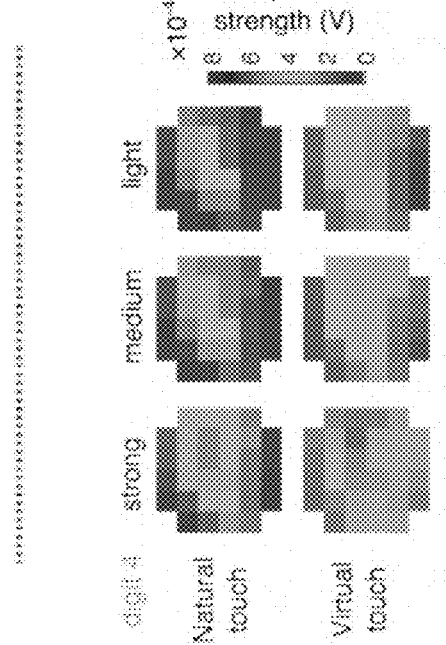

FIGS. 5a-b show examples of the spatial responses from two different sites (digit 1, digit 4) on the rat hand. Displayed are the maximum negative deviations in the trial-averaged virtual and natural touches. Each channel of the S1 recording array is shown in its actual spatial arrangement. Qualitatively, natural taction of the sites d1 and d4 activated two overlapping but clearly distinct zones. The optimized ITMS preserved this spatial pattern of activity for these two touch sites.

We compared the accuracy that the optimization procedure achieves experimentally with the accuracy of the theoretical model output. Theoretical reproduction accuracy under the linear model was significantly higher than the actual accuracy when tested over data from all animals. However, this trend was not observed in all animals separately. FIG. 5c shows this model vs. in-vivo comparison for all 4 animals. FIG. 5d shows, for a representative animal, a comparison (natural vs. optimized ITMS) of the energy output of S1, where we define the energy as the combined RMS voltage of the multichannel response in the response window. Generally, the response energy for each natural touch type was well matched by its ITMS counterpart ($r=0.81\pm0.13$).

Trial-Shuffling Analysis of Reproduction Accuracy

On a single-trial basis it is important that the evoked responses from virtual touch give an accurate representation of the natural touch. We quantified the single-trial accuracy by computing the distribution of the correlation coefficients between pairs of responses, whereas in the previous section, the accuracy of the trial-averaged response was quantified.

To compare two different sets of stereotyped trials, each individual trial response was randomly paired with a response in the other set 200 times. For each pairing a similarity score was computed and the average similarity score across random pairings was taken.

The following two empirical score distributions were calculated:
  matched virtual: Comparing virtual touch trials with natural touch trials of the same condition.
  condition-shuffled natural: Comparing natural touch trials with natural touch trials but with shuffled conditions (touch duration, strength, site).

In this example, the similarity score used was the correlation coefficient (r) of the spatiotemporal LFP responses. Over all trials in all animals, the matched virtual accuracy had a median of $r=0.5678\pm0.175$. Table 2 lists performances individually for each animal and site.

The result of this analysis was that the natural touch responses were better mimicked by virtual touch than condition-shuffled natural responses. Across all touch conditions in all animals, the condition-shuffled scores were found to be significantly lower (p=0.017 one tailed sign test) than the matched virtual scores. The scores were also found to be much higher when only considering a post-touch-onset window of 100 ms (p<0.01).

Figures 6A, 6B:
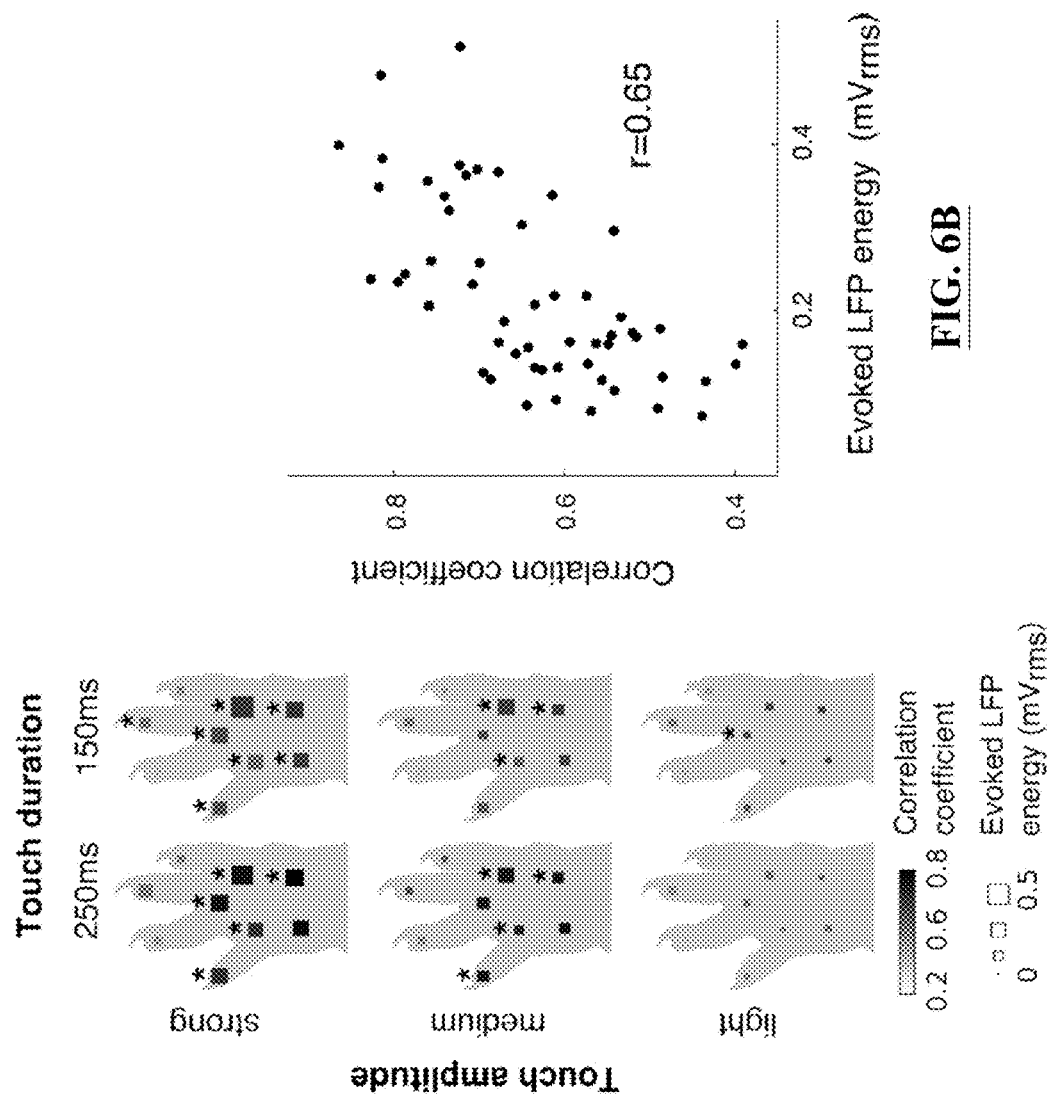
FIG. 6A and FIG. 6B single-trial accuracy and response magnitude organized by touch site and pattern.

FIG. 6a shows the accuracy scores for each touch condition for a representative animal. FIG. 6b shows, for the same experiment, that the reproduction performance was dependent on the total magnitude of the overall LFP response. Table 2 lists these scores individually for each touch site. The last column of the table shows the significance levels $p_{mimic}$ for detecting an improvement of the matched virtual over condition-shuffled natural across all trials at a touch site.

Classification Performance

To assess the information content of virtual touch responses, we performed a set of classification experiments in which the touch condition (duration, location, amplitude) was predicted from multichannel peristimulus responses. First, we trained a separate classifier for natural touch responses and for virtual touch responses. The classification rates in this scenario tell us how much information the neural response provides about each stimulus modality in isolation. Then we tested a more generalized classifier that could correctly determine the touch conditions for both natural and virtual touch responses. The motivation behind this experiment was to see how well virtual touch responses contained touch parameter discriminability while simultaneously mimicking natural responses.

TABLE 2

Performance statistics for all touch sites attempted on all animals. The maximum current applied by the controller is shown in the third column. Mean and s. d. accuracy is shown in columns 4-6. $p_{mimic}$ is the significance level for detecting an improvement of matched virtual over condition-shuffled natural across all trials at a touch site. Bold rows correspond with touch sites whose $p_{mimic}$ was less than 0.05.

| Ani-mal | Touch site | Max current (µA) | trial average | matched virtual | condition-shuff. natural | $p_{mimic}$ |
|---|---|---|---|---|---|---|
| A | d1 | 13.90 | 0.88 ± 0.03 | 0.65 ± 0.13 | 0.61 ± 0.12 | 0.0207 |
|   | p1 | 12.61 | 0.79 ± 0.12 | 0.43 ± 0.24 | 0.62 ± 0.15 | 1.0000 |
|   | mp | 16.87 | 0.91 ± 0.03 | 0.62 ± 0.16 | 0.62 ± 0.13 | 1.0000 |
| B | d1 | 15.13 | 0.91 ± 0.04 | 0.60 ± 0.11 | 0.55 ± 0.10 | 0.0000 |
|   | d2 | 16.63 | 0.73 ± 0.14 | 0.57 ± 0.17 | 0.59 ± 0.12 | 0.000 |
|   | d3 | 11.82 | 0.82 ± 0.06 | 0.55 ± 0.10 | 0.61 ± 0.09 | 1.0000 |
|   | d4 | 15.41 | 0.71 ± 0.09 | 0.43 ± 0.22 | 0.43 ± 0.19 | 0.0000 |
|   | p3 | 25.00 | 0.80 ± 0.07 | 0.67 ± 0.09 | 0.60 ± 0.08 | 0.0000 |
|   | p1 | 21.57 | 0.90 ± 0.04 | 0.60 ± 0.13 | 0.58 ± 0.12 | 0.0013 |
|   | mp | 17.10 | 0.78 ± 0.12 | 0.61 ± 0.14 | 0.58 ± 0.10 | 0.0000 |
| C | d1 | 15.13 | 0.61 ± 0.17 | 0.38 ± 0.22 | 0.39 ± 0.14 | 0.0023 |
|   | d2 | 16.63 | 0.73 ± 0.11 | 0.42 ± 0.16 | 0.44 ± 0.12 | 0.0028 |
|   | d3 | 11.82 | 0.77 ± 0.10 | 0.39 ± 0.15 | 0.40 ± 0.14 | 0.0000 |
|   | d4 | 15.41 | 0.89 ± 0.02 | 0.53 ± 0.11 | 0.52 ± 0.10 | 0.0000 |
|   | p1 | 25.00 | 0.89 ± 0.02 | 0.62 ± 0.13 | 0.55 ± 0.11 | 0.0000 |
|   | p2 | 21.57 | 0.80 ± 0.07 | 0.59 ± 0.15 | 0.52 ± 0.10 | 0.0000 |
|   | p3 | 17.10 | 0.91 ± 0.03 | 0.56 ± 0.14 | 0.52 ± 0.11 | 0.1436 |
|   | lp | 17.42 | 0.87 ± 0.05 | 0.56 ± 0.12 | 0.55 ± 0.09 | 0.0000 |
|   | mp | 19.86 | 0.90 ± 0.03 | 0.62 ± 0.12 | 0.54 ± 0.11 | 0.0000 |
| D | d1 | 15.13 | 0.84 ± 0.15 | 0.48 ± 0.18 | 0.58 ± 0.11 | 1.0000 |
|   | d2 | 16.63 | 0.84 ± 0.09 | 0.53 ± 0.15 | 0.56 ± 0.14 | 1.0000 |
|   | d3 | 11.82 | 0.74 ± 0.11 | 0.60 ± 0.17 | 0.62 ± 0.11 | 0.5000 |
|   | d4 | 15.41 | 0.77 ± 0.10 | 0.61 ± 0.19 | 0.61 ± 0.13 | 0.8203 |
|   | p1 | 25.00 | 0.79 ± 0.12 | 0.60 ± 0.18 | 0.61 ± 0.12 | 0.0030 |
|   | p2 | 21.57 | 0.81 ± 0.10 | 0.63 ± 0.17 | 0.60 ± 0.12 | 0.0000 |
|   | p3 | 17.10 | 0.76 ± 0.09 | 0.50 ± 0.22 | 0.49 ± 0.16 | 0.0001 |
|   | mp | 17.42 | 0.84 ± 0.08 | 0.64 ± 0.14 | 0.60 ± 0.12 | 0.0000 |
|   | lp | 19.86 | 0.83 ± 0.10 | 0.53 ± 0.16 | 0.60 ± 0.12 | 1.0000 |

The classification procedure was as follows: We assumed the LFP responses given the label were unimodal. Under this assumption, each sample could be assigned the label of the nearest peristimulus average. To take into account covariance, linear discriminant analysis (LDA) was used to project the responses into a lower dimensional subspace. LDA has a closed form solution given by a generalized eigenvalue problem defined by the between-class and within-class covariance matrices. Since the responses had many dimensions (300 ms×$F_s$×32 channels), principal component analysis (PCA) was performed before computing the covariance matrices. Then each response was projected into a reduced subspace before being assigned the label of the nearest peristimulus average. In the following, we chose the reduced dimensionality by cross validation, but it is at most one less than the number of classes.

For the generalized classifier, natural and virtual touches were used in computing the LDA projection, but the final classification was based on the label of the nearest natural touch mean. This ensures that the virtual touch response is indeed closest to the corresponding natural touch peristimulus average.

Table 3 shows the classification performance resulting from both the individually trained classifiers and the single generalized classifier. Table 4 shows the same rate for classifying touch location when only considering trials of strong stimuli and short (150 ms) duration. It is clear that for this particular subset of data, the classification rates for the single generalized classifier are close to the rates for the individually trained natural touch classifier for both natural and virtual touch.

Figures 7A, 7B, 7C:
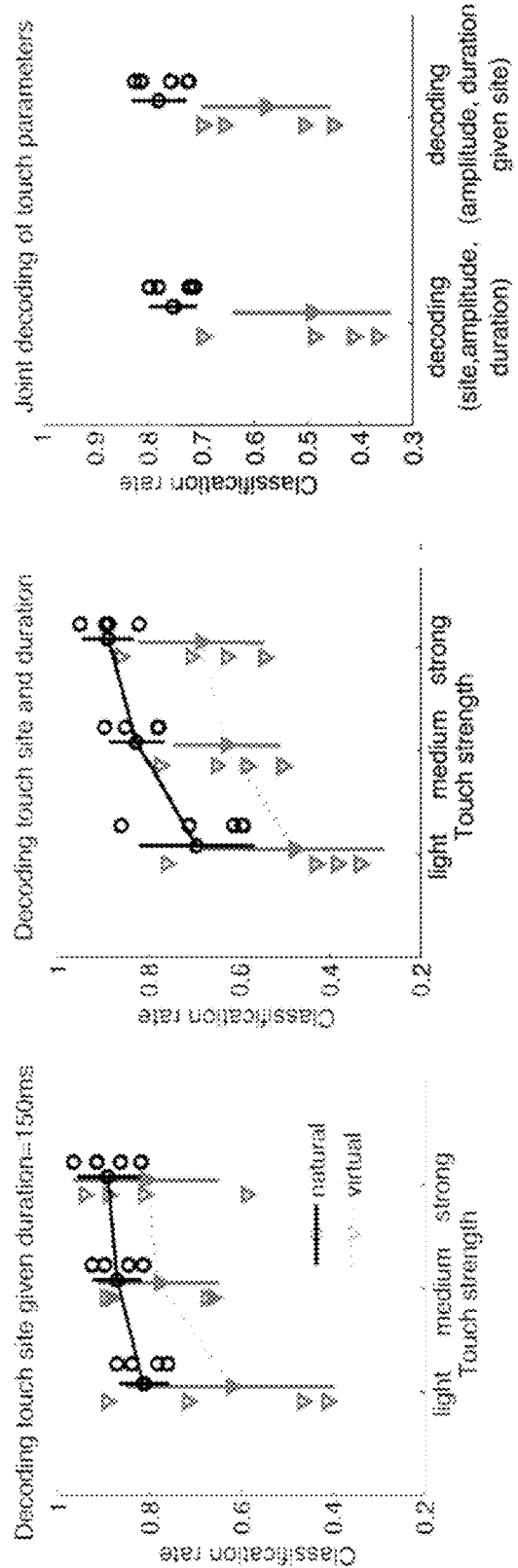
FIG. 7A, FIG. 7B, and FIG. 7C show correct touch decoding rates using a generalized classifier. The classifier was trained on both virtual and natural touch responses, but predictions were made by comparison with natural touch means. Classification rate is calculated as the (# of correctly classified trials)/(total # of trials) computed over 8 Monte-Carlo selections of training/test data (⅔ train, ⅓ test). Data points represent animals. Error bars show ±1 s.d. across animals.

FIGS. 7a and 7b show classification rates based on two other restricted subsets of trials. FIG. 7a shows correct decoding rates for the subsets of data corresponding to light, medium, or strong touches of short (150 ms) duration. FIG. 7b similarly shows rates for decoding touch site and duration when considering only light, medium, or strong trials. The first column of FIG. 7c shows decoding performance when considering all types of trials, and the second column shows the overall accuracy when considering site-conditional subsets of data.

Shown beside these heatmaps is the corresponding spatial pattern of spiking on the same electrodes. As the touch site is varied from one side of the hand to the other, the charge injected on each electrode, as well as native spiking, follows a spatial progression from medial to lateral on the VPL array. The spatial topology of the natural responses also follows a slight progression from posterior to anterior—a pattern that is roughly replicated by the virtual touch responses.

TABLE 3

Correct classification rates for decoding touch parameters (touch site, duration, amplitude) from responses to natural and virtual touch. The mean and standard deviation of the rates across 8 Monte-Carlo divisions of data (⅔ train, ⅓ test) are shown. The individually trained classifiers used trial data from exclusively natural or virtual touch, while the dimensionality reduction for the joint classifier was trained with trials from both sets, and test examples are classified by selecting the nearest natural touch mean. The chance levels of prediction, which are dependent on the number of touch sites attempted on each animal, are shown in the second column.

| | | Trained separately | | | | Generalized classifier | | | |
|---|---|---|---|---|---|---|---|---|---|
| | | natural | | virtual | | natural | | virtual | |
| Animal | chance | mean | s.d. | mean | s.d. | mean | s.d. | mean | s.d. |
| A | 0.0556 | 0.759 | 0.028 | 0.5354 | 0.0285 | 0.7229 | 0.0288 | 0.4127 | 0.0357 |
| B | 0.0238 | 0.8422 | 0.0114 | 0.8125 | 0.0177 | 0.7964 | 0.016 | 0.698 | 0.0169 |
| C | 0.0185 | 0.7984 | 0.0205 | 0.6711 | 0.0142 | 0.7807 | 0.0155 | 0.3668 | 0.018 |
| D | 0.0185 | 0.7606 | 0.023 | 0.7692 | 0.018 | 0.714 | 0.0161 | 0.487 | 0.0215 |
| average | | 0.79508 | | 0.70766 | | 0.75756 | | 0.48588 | |

TABLE 4

Decoding touch site given a short, strong touch. Correct classification rates here reflect the discriminability endowed by spatial variation in natural and/or virtual stimuli. Similar to Table 3, the chance levels are shown in the second column. The means and standard deviations shown are with respect to 8 Monte-Carlo trial divisions (⅔ train, ⅓ test).

| | | Trained separately | | | | Generalized classifier | | | |
|---|---|---|---|---|---|---|---|---|---|
| | | natural | | virtual | | natural | | virtual | |
| Animal | chance | mean | s.d. | mean | s.d. | mean | s.d. | mean | s.d. |
| A | 0.3333 | 0.9764 | 0.0226 | 0.8889 | 0.0526 | 0.9653 | 0.0199 | 0.8889 | 0.046 |
| B | 0.1429 | 0.957 | 0.0237 | 0.975 | 0.0179 | 0.9141 | 0.0289 | 0.9422 | 0.0227 |
| C | 0.1111 | 0.9271 | 0.036 | 0.7931 | 0.0535 | 0.8625 | 0.0379 | 0.5882 | 0.0623 |
| D | 0.1111 | 0.8205 | 0.0424 | 0.9016 | 0.0412 | 0.818 | 0.046 | 0.8123 | 0.045 |
| average | | 0.9073 | | 0.8944 | | 0.8789 | | 0.8059 | |

Optimized Pattern Characteristics

We examined the output of the model predictive controller in terms of the timing of pulses and their spatial properties. VPL spatial current injection for different touch sites followed a somatotopic progression from medial to lateral as the touch site varied from lateral to medial on the hand. Any given virtual touch primarily used 1-3 bipolar configurations (2-6 stimulating electrodes), and the number of configurations used across all touch sites spanned 4-5 configurations. Most of the pulses occurred in a short burst from 4-8 ms after onset. This coincides with observations that the initial response latency to taction is ~9 ms, and the latency of VPL stimulation is ~2 ms. The maximum pulse amplitudes are shown in Table 2 for each touch site.

Figure 8:
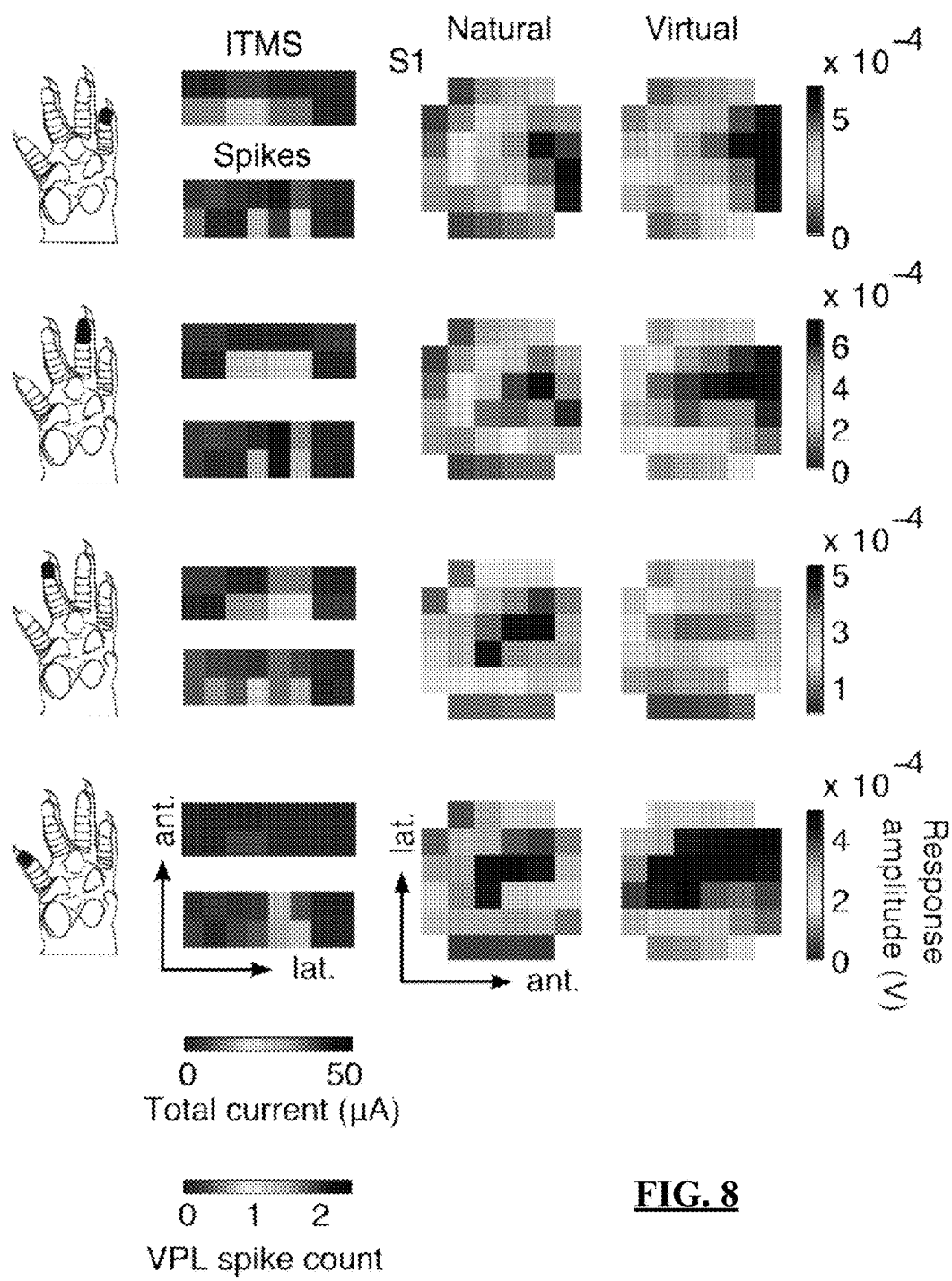
FIG. 8 shows spatial distribution of current injection and response amplitudes for optimized microstimulation versus natural touch. For the 4 touch sites displayed on the left column, the second column shows the distribution of current injection on the VPL electrode array and the accompanying average spike counts on the same electrodes. Spatially, the optimized current injection pattern coincides with the locations of responsive units. The heat maps show the natural and virtual response topologies in S1 for a medium-strength touch of 250 ms duration. Here, we define the response amplitude as the absolute value of the most negative voltage in the trial-average LFP.

FIG. 8 shows a representative example of the spatial variation of current injection as a function of touch site.

Optimized ITMS Resembles Spatiotemporal VPL Spiking

Figures 9A, 9B:
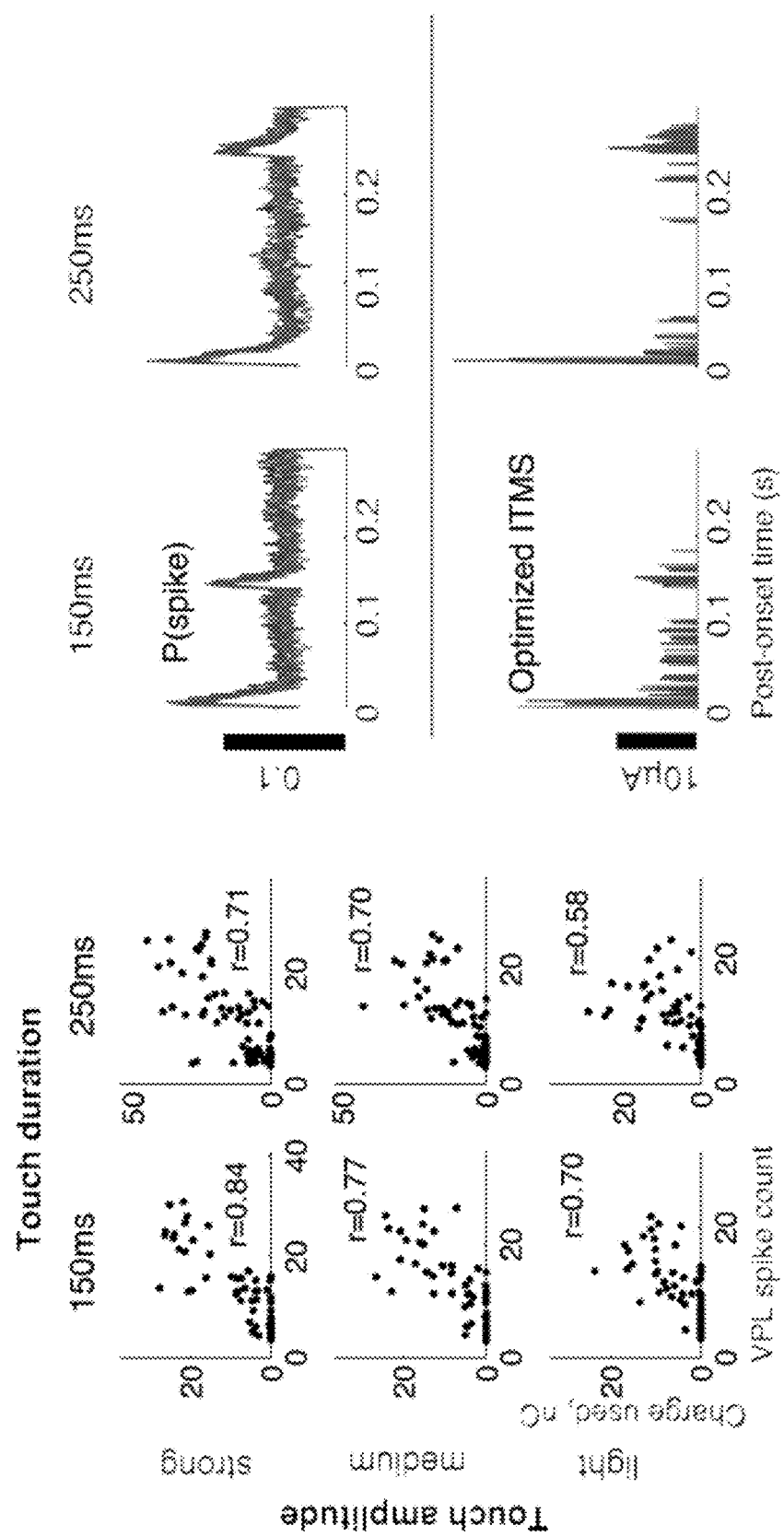
FIG. 9A and FIG. 9B show spatial and temporal correlation with natural VPL spiking.

One topic of interest is how closely the optimized ITMS patterns resembled single-unit activity measured on the stimulating electrodes. Spatially, charge was injected primarily through electrodes whose neurons were found to be touch-responsive. FIG. 9a shows the relationship between natural VPL spiking and total stimulation current during virtual touch for a representative animal. For each touch condition, the total spike count in the first 150 ms following touch onset for a given electrode is plotted with respect to the total charge injection through that electrode. The strongest correlation was observed for the high-amplitude touch conditions ($r=0.84$ for 150 ms touches and $r=0.71$ for 250 ms touches).

FIG. 9b shows, for two different touch durations, the post-onset spike rate and the corresponding optimized ITMS. For each time point, the displayed waveforms are the maximum currents across channels. The strongest stimulation pulses were delivered shortly after touch onset and offset. This resembled the natural temporal pattern of VPL spike rate in that almost all touch-responsive units recorded showed rapid adaptation.

Summary of Example Results

Some aspects of the subject technology involve a neurophysiological approach to encoder design that optimizes the naturalness of downstream evoked responses. This provides a way to directly compute extremely detailed spatiotemporal microstimulation waveforms that, according to a model of activation, are optimal for evoking desired natural responses.

The optimized microstimulation patterns accurately evoke LFPs resembling touch-evoked responses. This was tested over a range of amplitudes and patterns. Overall, the waveforms that resulted from this optimization shared some notable characteristics: 1) For the physical contact area used, (1 mm$^2$), most of the optimized ITMS patterns used 1-3 electrode configurations over the course of 300 ms following touch onset, and these configurations were usually adjacent to each other. 2) Temporally, the optimized ITMS consisted of a brief burst of pulses beginning 5-7 ms after touch onset and a secondary burst of pulses shortly after touch release. In between these two bursts, the amount of charge injected in the holding period was negligible. 3) The stimulation amplitudes (with stereotyped biphasic pulses with 200 µs per phase) largely remained below the 25 µA limit, although in some cases this bound was reached.

The accuracy scores were also related to the goodness-of-fit of the linear models, which in turn was dependent on signal quality and implant placement. Reproduction accuracy also followed a somatotopic trend, suggesting that the spatial reproduction capability was limited by our array placement and/or resolution.

Linear and Nonlinear Models

Neural responses to both thalamic and cortical microstimulation have been shown to be nonlinear. In addition, this non linearity is time-varying since after the initial microstimulation the microstimulation amplitude to neural response amplitude function changes greatly for times later in the response. Although more accurate models of activation could be trained, they are more computationally burdensome to control—often without assurance of optimality. Since MPC is globally optimal for linear models, inaccuracies in our case were likely due to unmodeled nonlinear effects. This is further supported by the fact that the animals whose linear models had the highest goodness-of-fit also had better control performance. Although some embodiments of the subject technology have been described as employing linear models, nonlinear models can be used instead of linear models in some embodiments.

Although, as a control system, certain disclosed methods do not incorporate feedback, i.e., are open-loop, the subject technology can be implemented in some embodiments with closed-loop strategies, e.g., similar to the work of Potter et al (2005), for reproducing sensory responses with microstimulation. Although closed-loop control may improve control performance, naive implementations could inadvertently reduce naturally occurring response variability, which could be the result of important thalamocortical processing/plasticity, such as motor inhibition and gating.

Obtaining Natural Templates

Subject-specific neural responses to natural stimuli would not be available in a somatosensory prosthetic setting, since the target population for such a device would, by definition, lack intact somatosensory representation. This sort of problem is definitely not unique to sensory neural prostheses. Some work on motor brain-machine interfaces uses intact limb kinematics in nonhuman primates to initialize models that map neural firing to limb kinematics and/or force. More recently, studies on hippocampal prosthetics such as those conducted by Berger et al. require full observation of neural firing from input and output populations to train a mapping.

Nevertheless, the patterns that result from fully observed experiments such as these can provide insights into generalizable spatiotemporal patterns. Some aspects of the subject technology involve identification of stimulation properties that are consistent across experimental subjects. This could lead to the subsequent design of sophisticated dynamical encoders whose parameters are largely optimized offline with some non-generalizable parameters that can be calibrated by the user. For example, since the limb representations of VPL and S1 are somatopically organized it is possible that cross-subject or cross-species generalization could amount to a simple intensity scaling and/or spatial remapping. These calibrations could also be optimized under a reinforcement learning framework.

Associating Pre-Defined Microstimulation Patterns

Some authors have studied the discriminability of pulse train characteristics. These experiments individually tested parameters of pulse trains such as relative amplitude, train frequency, level of temporal randomness, and spatiotemporal aspects. The patterns, however, were heuristically chosen stereotyped trains, usually involving just one electrode at a time, whose actual percepts are unknown. When these types of trains were applied to human subjects' VPL nucleus, they reported for the most part unnatural sensations.

These sorts of pulse trains have been shown to mimic at least some aspects of tactile perception, such as flutter frequency, intensity, and spatial location to the extent that a natural stimulus and a microstimulation train can be compared on the same scale. For example, Berg et al. (2013) and Tabot et al. (2013) demonstrated an encoder that performs static conversion from skin indentation force and microstimulation amplitude. The pulse pattern was a constant amplitude, constant frequency train, applied through a single electrode, and the nonlinear amplitude conversion was performed by psycho metric equivalence. This means that the amplitude was tuned based on binary comparisons (e.g. "more intense than" or "more medial than") with natural skin indentations. This encoder matches amplitudes. Relative to some prior techniques, some aspects of the subject technology provide a more general class of dynamic, spatiotemporal encoders that improve naturalness and information throughput. As the parametric complexity of the encoders grows, however, the difficulty of psychometric calibration in animal models increases.

Emulating the Neural Code in the Stimulation Area

Other groups have shown that an encoder that mimics the natural spiking activity of an implanted region can evoke realistic downstream spiking or restore cognitive ability by playback of recorded single unit activity or forward point process modeling. However, the subject technology differs in the sense that the stimulation is not optimized to explicitly mimic the response in the stimulated brain region, but rather to evoke downstream responses close to some templates. Interestingly, in post-hoc analysis we have found the patterns of microstimulation correlate with the stimulated areas spiking.

Using microstimulation pulses that explicitly mimic single-unit patterns in the stimulation region can have unintended consequences, as microstimulation pulses have been shown to activate neural elements that are not directly measurable from single-unit recordings, such as fibers of passage. A microstimulation pulse may be a poor substitute for a natural spike recorded from the same channel. With each pulse, it is hard to ascertain how many cells were activated, and it has been shown that the projection fields of stimulating pulses—the somatotopic topology of their downstream responses—are offset from the receptive fields on units recorded on the same electrodes. An advantage in some embodiments of the subject technology is that is that the optimization approach employed can account for these effects.

Model-based "control" is equivalent, under some assumptions, to model-based stimulus decoding, which has been extensively studied in the neuroscience community.

Maximizing the Information Rate of Microstimulation

An interesting approach by Daly et al., 2012, poses microstimulation patterning as a channel coding problem, designing a transduction filter that maximizes the mutual information between external stimuli and the neural response (in a neural model of the thalamocortical system). Some methods of the subject technology, in contrast, do not explicitly optimize information metrics. Objectives of information transfer and naturalness of the responses could yield similar results. However, one could argue that a perfectly biomimetic encoder would yield the same mutual information that exists in the intact neural system, which would be more than sufficient for a prosthetic device. One could also imagine encoders with very high information transfer but with a very unnatural spatiotemporal mapping. At least in an asymptotic sense, a biomimetic approach seems more appropriate for neural prosthetic applications. Here we have shown that the LFPs responses to both natural and virtual touch are quite informative about the touch with an average accuracy of 79.5% and 70.8%, respectively, in decoding the joint parameters corresponding to site, amplitude, and duration. Given a strong short touch, the touch sites were accurately predicted with averages of 90.7% and 89.4%, respectively. This demonstrates the microstimulation evoked responses are both highly informative and naturalistic.

Systems

Figure 10:
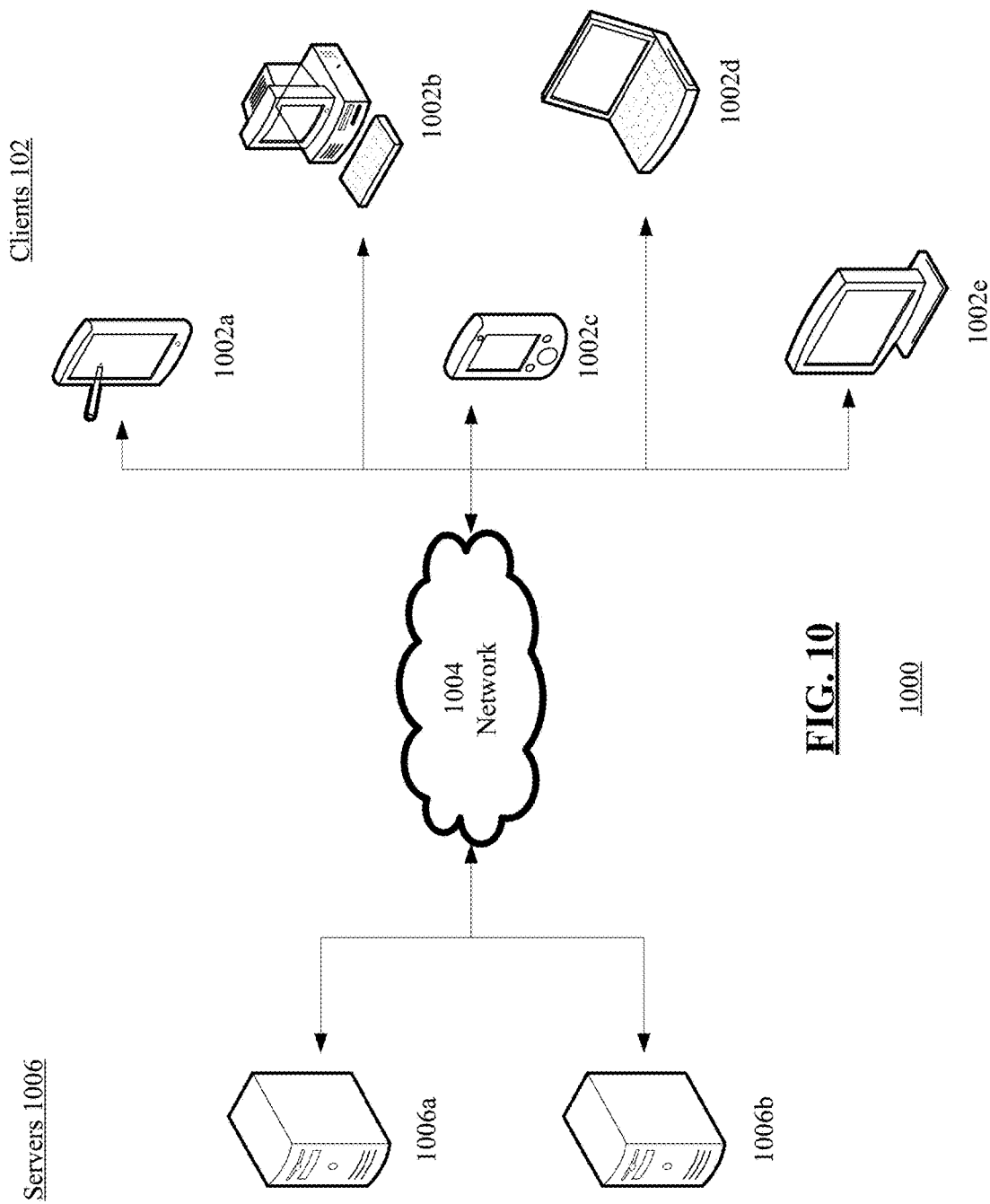
FIG. 10 is an exemplary diagram of a network in which systems and methods herein may be implemented.

FIG. 10 is a simplified diagram of a system 1000, in accordance with various embodiments of the subject technology. The system 1000 may include one or more remote client devices 1002 (e.g., client devices 1002a, 1002b, 1002c, 1002d, and 1002e) in communication with one or more server computing devices 1006 (e.g., servers 1006a and 1006b) via network 1004. In some embodiments, a client device 1002 is configured to run one or more applications based on communications with a server 1006 over a network 1004. In some embodiments, a server 1006 is configured to run one or more applications based on communications with a client device 1002 over the network 1004. In some embodiments, a server 1006 is configured to run one or more applications that may be accessed and controlled at a client device 1002. For example, a user at a client device 1002 may use a web browser to access and control an application running on a server 1006 over the network 1004. In some embodiments, a server 1006 is configured to allow remote sessions (e.g., remote desktop sessions) wherein users can access applications and files on a server 1006 by logging onto a server 1006 from a client device 1002. Such a connection may be established using any of several well-known techniques such as the Remote Desktop Protocol (RDP) on a Windows-based server.

By way of illustration and not limitation, in some embodiments, stated from a perspective of a server side (treating a server as a local device and treating a client device as a remote device), a server application is executed (or runs) at a server 1006. While a remote client device 1002 may receive and display a view of the server application on a display local to the remote client device 1002, the remote client device 1002 does not execute (or run) the server application at the remote client device 1002. Stated in another way from a perspective of the client side (treating a server as remote device and treating a client device as a local device), a remote application is executed (or runs) at a remote server 1006.

By way of illustration and not limitation, in some embodiments, a client device 1002 can represent a desktop computer, a mobile phone, a laptop computer, a netbook computer, a tablet, a thin client device, a personal digital assistant (PDA), a portable computing device, and/or a suitable device with a processor. In one example, a client device 1002 is a smartphone (e.g., iPhone, Android phone, Blackberry, etc.). In certain configurations, a client device 1002 can represent an audio player, a game console, a camera, a camcorder, a Global Positioning System (GPS) receiver, a television set top box an audio device, a video device, a multimedia device, and/or a device capable of supporting a connection to a remote server. In some embodiments, a client device 1002 can be mobile. In some embodiments, a client device 1002 can be stationary. According to certain embodiments, a client device 1002 may be a device having at least a processor and memory, where the total amount of memory of the client device 1002 could be less than the total amount of memory in a server 1006. In some embodiments, a client device 1002 does not have a hard disk. In some embodiments, a client device 1002 has a display smaller than a display supported by a server 1006. In some aspects, a client device 1002 may include one or more client devices.

In some embodiments, a server 1006 may represent a computer, a laptop computer, a computing device, a virtual machine (e.g., VMware® Virtual Machine), a desktop session (e.g., Microsoft Terminal Server), a published application (e.g., Microsoft Terminal Server), and/or a suitable device with a processor. In some embodiments, a server 1006 can be stationary. In some embodiments, a server 1006 can be mobile. In certain configurations, a server 1006 may be any device that can represent a client device. In some embodiments, a server 1006 may include one or more servers.

In some embodiments, a first device is remote to a second device when the first device is not directly connected to the second device. In some embodiments, a first remote device may be connected to a second device over a communication network such as a Local Area Network (LAN), a Wide Area Network (WAN), and/or other network.

When a client device 1002 and a server 1006 are remote with respect to each other, a client device 1002 may connect to a server 1006 over the network 1004, for example, via a modem connection, a LAN connection including the Ethernet or a broadband WAN connection including DSL, Cable, T1, T3, Fiber Optics, Wi-Fi, and/or a mobile network connection including GSM, GPRS, 3G, 4G, 4G LTE, WiMax or other network connection. Network 1004 can be a LAN network, a WAN network, a wireless network, the Internet, an intranet, and/or other network. The network 1004 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name, and/or other system name. These illustrate some examples as to how one device may be remote to another device, but the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or server computer or like terms.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

Figure 11:
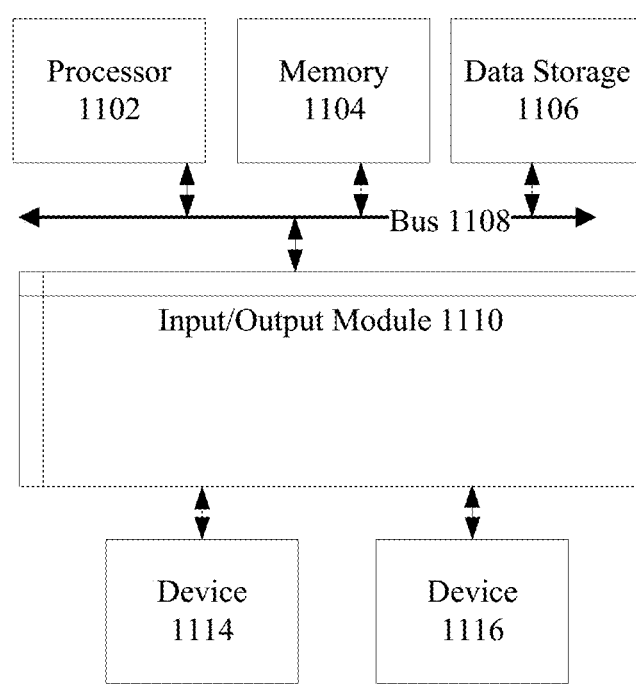
FIG. 11 is an exemplary diagram of a client or server of FIG. 10.

FIG. 11 is a block diagram illustrating an exemplary computer system 1100 with which a client device 1002 and/or a server 1006 of FIG. 10 can be implemented. In certain embodiments, the computer system 1100 may be implemented using hardware or a combination of software and hardware, either in a dedicated server, or integrated into another entity, or distributed across multiple entities.

The computer system 1100 (e.g., client 1002 and servers 1006) includes a bus 1108 or other communication mechanism for communicating information, and a processor 1102 coupled with the bus 1108 for processing information. By way of example, the computer system 1100 may be implemented with one or more processors 1102. The processor 1102 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, and/or any other suitable entity that can perform calculations or other manipulations of information.

The computer system 1100 can include, in addition to hardware, code that creates an execution environment for the computer program in question, e.g., code that constitutes processor firmware, a protocol stack, a database management system, an operating system, or a combination of one or more of them stored in an included memory 1104, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, and/or any other suitable storage device, coupled to the bus 1108 for storing information and instructions to be executed by the processor 1102. The processor 1102 and the memory 1104 can be supplemented by, or incorporated in, special purpose logic circuitry.

The instructions may be stored in the memory 1104 and implemented in one or more computer program products, i.e., one or more modules of computer program instructions encoded on a computer readable medium for execution by, or to control the operation of, the computer system 1100, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and/or application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and/or xml-based languages. The memory 1104 may also be used for storing temporary variable or other intermediate information during execution of instructions to be executed by the processor 1102.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The computer system 1100 further includes a data storage device 1106 such as a magnetic disk or optical disk, coupled to the bus 1108 for storing information and instructions. The computer system 1100 may be coupled via an input/output module 1110 to various devices (e.g., devices 1114 and 1116). The input/output module 1110 can be any input/output module. Exemplary input/output modules 1110 include data ports (e.g., USB ports), audio ports, and/or video ports. In some embodiments, the input/output module 1110 includes a communications module. Exemplary communications modules include networking interface cards, such as Ethernet cards, modems, and routers. In certain aspects, the input/output module 1110 is configured to connect to a plurality of devices, such as an input device 1114 and/or an output device 1116. Exemplary input devices 1114 include a keyboard and/or a pointing device (e.g., a mouse or a trackball) by which a user can provide input to the computer system 1100. Other kinds of input devices 1114 can be used to provide for interaction with a user as well, such as a tactile input device, visual input device, audio input device, and/or brain-computer interface device. For example, feedback provided to the user can be any form of sensory feedback (e.g., visual feedback, auditory feedback, and/or tactile feedback), and input from the user can be received in any form, including acoustic, speech, tactile, and/or brain wave input. Exemplary output devices 1116 include display devices, such as a cathode ray tube (CRT) or liquid crystal display (LCD) monitor, for displaying information to the user.

According to certain embodiments, a client device 1002 and/or server 1006 can be implemented using the computer system 1100 in response to the processor 1102 executing one or more sequences of one or more instructions contained in the memory 1104. Such instructions may be read into the memory 1104 from another machine-readable medium, such as the data storage device 1106. Execution of the sequences of instructions contained in the memory 1104 causes the processor 1102 to perform the process steps described herein. One or more processors in a multi-processing arrangement may also be employed to execute the sequences of instructions contained in the memory 1104. In some embodiments, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., a data server), or that includes a middleware component (e.g., an application server), or that includes a front end component (e.g., a client computer having a graphical user interface and/or a Web browser through which a user can interact with an implementation of the subject matter described in this specification), or any combination of one or more such back end, middleware, or front end components. The components of the system 1100 can be interconnected by any form or medium of digital data communication (e.g., a communication network). Examples of communication networks include a local area network and a wide area network.

The term "machine-readable storage medium" or "computer readable medium" as used herein refers to any medium or media that participates in providing instructions to the processor 1102 for execution. Such a medium may take many forms, including, but not limited to, non-volatile media, volatile media, and transmission media. Non-volatile media include, for example, optical or magnetic disks, such as the data storage device 1106. Volatile media include dynamic memory, such as the memory 1104. Transmission media include coaxial cables, copper wire, and fiber optics, including the wires that comprise the bus 1108. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, a "processor" can include one or more processors, and a "module" can include one or more modules.

In an aspect of the subject technology, a machine-readable medium is a computer-readable medium encoded or stored with instructions and is a computing element, which defines structural and functional relationships between the instructions and the rest of the system, which permit the instructions' functionality to be realized. Instructions may be executable, for example, by a system or by a processor of the system. Instructions can be, for example, a computer program including code. A machine-readable medium may comprise one or more media.

Figure 12:
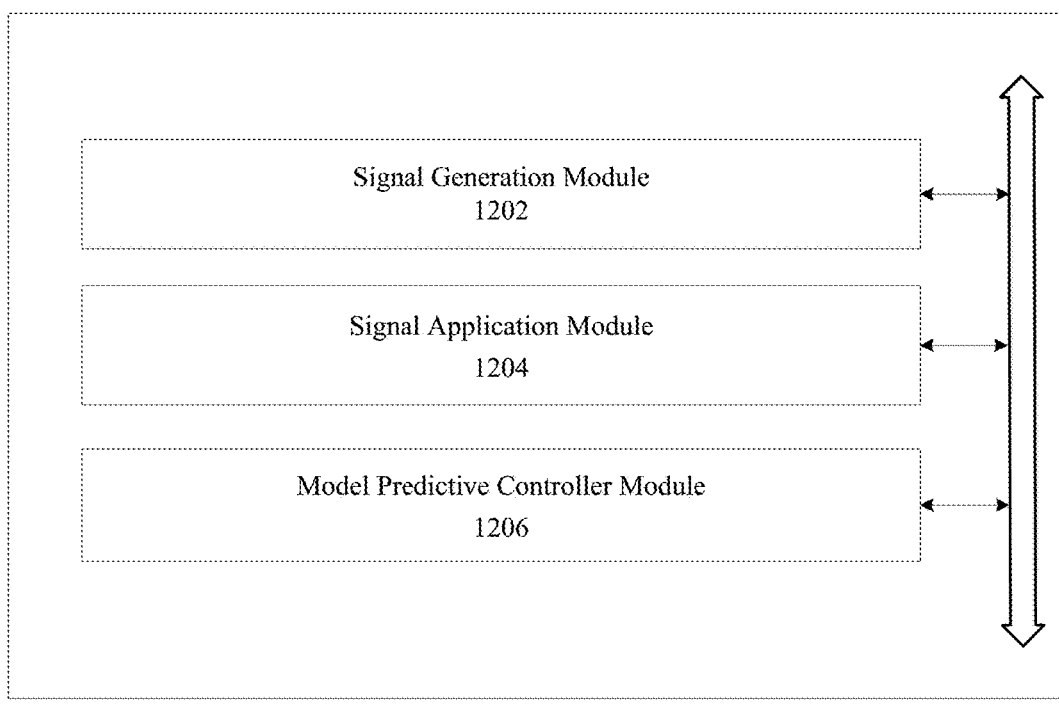
FIG. 12 is an exemplary diagram of modules implementing methods of the subject technology.

FIG. 12 illustrates an example of a system 1200 for delivering sensory information to a subject mammal, in accordance with various embodiments of the subject technology. The system 1200 is an example of an implementation of a client device 1002 and/or a server 1006 for delivering sensory information to a subject mammal. The system 1200 comprises a signal generation module 1202, a signal application module 1204, and/or a model predictive controller module 1206. Although the system 1200 is shown as having these modules, the system 1200 may have other suitable configurations. The modules of the system 1200 may be in communication with one another. In some embodiments, the modules may be implemented in software (e.g., subroutines and code). For example, the modules may be stored in the memory 1104 and/or data storage 1106, and executed by the processor 1102. In some aspects, some or all of the modules may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices) and/or a combination of both. Additional features and functions of these modules according to various aspects of the subject technology are further described in the present disclosure.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

Figure 13:
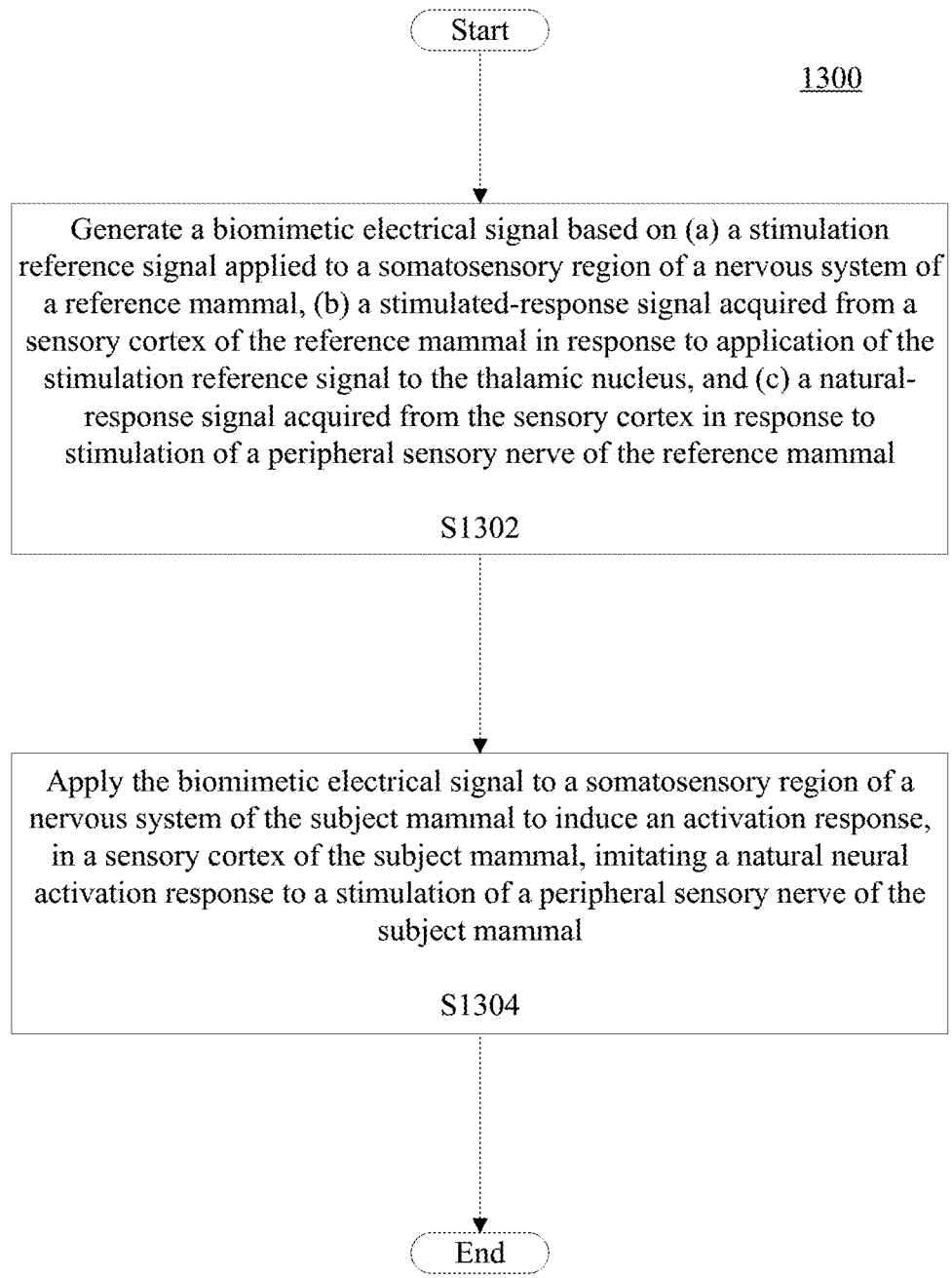
FIG. 13 is a flowchart of exemplary processing according to some methods and systems of the subject technology.

FIG. 13 illustrates an example of a method 1300 for delivering sensory information to a subject mammal, in accordance with various embodiments of the subject technology. The method 1300 is an example of an implementation of system 1200 for delivering sensory information to a subject mammal. The method 1300 comprises an operation s1302 to generate a biomimetic electrical signal based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to stimulation of a peripheral sensory nerve of the reference mammal. The method 1300 further comprises an operation s1304 to apply the biomimetic electrical signal to a somatosensory region of a nervous system of the subject mammal to induce an activation response, in a sensory cortex of the subject mammal, imitating a natural neural activation response to a stimulation of a peripheral sensory nerve of the subject mammal.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A system for delivering sensory information to a subject mammal, the system comprising:
   a signal generation module configured to generate a biomimetic electrical signal based on (a) a stimulation reference signal applied to a somatosensory region of a nervous system of a reference mammal, (b) a stimulated-response signal acquired from a sensory cortex of the reference mammal in response to application of the stimulation reference signal to the thalamic nucleus, and (c) a natural-response signal acquired from the sensory cortex in response to peripheral touch stimuli and/or peripheral nerve stimulation of the reference mammal; and
   a signal application module configured to apply the biomimetic electrical signal to a somatosensory region of a nervous system of the subject mammal to induce an activation response, in a sensory cortex of the subject mammal.

2. The system of claim 1, wherein the applying of the biomimetic electrical signal is to a human.

3. The system of claim 1, wherein the reference mammal is the subject mammal.

4. The system of claim 1, wherein the reference mammal is a mammal other than the subject mammal.

5. The system of claim 4, wherein the subject mammal and the reference mammal are of different species.

6. The system of claim 1, wherein the biomimetic electrical signal is generated by a prosthetic device.

7. The system of claim 1, wherein the sensory cortex of each of the reference mammal and the subject mammal is a primary somatosensory cortex (S1).

8. The system of claim 1, wherein the somatosensory region of each of the reference mammal and the subject mammal comprises a primary somatosensory cortex.

9. The system of claim 8, wherein the somatosensory region of each of the reference mammal and the subject mammal comprises at least one of a Brodmann area 1, a Brodmann area 2, a Brodmann area 3b, a Brodmann area 3a and a somatosensory thalamic nucleus, such as a Ventral Posterior Lateral (VPL) nucleus of the thalamus, also called the Ventral Caudal (VC) nucleus in humans, or the proprioceptive thalamic region.

10. The system of claim 1, wherein the somatosensory region of the nervous system of each of the reference mammal and the subject mammal comprises a thalamic nucleus.

11. The system of claim 10, wherein the thalamic nucleus of each of the reference mammal and the subject mammal is a ventral posterior lateral thalamus, also called Ventral Caudal (VC) nucleus in humans.

12. The system of claim 1, wherein the peripheral sensory nerve of the subject mammal is in a limb of the subject mammal.

13. The system of claim 12, wherein the biomimetic electrical signal is applied to the thalamic nucleus of the subject mammal after the subject mammal has lost at least a portion of the limb.

14. The system of claim 1, wherein the natural-response reference signal is acquired from the sensory cortex of the reference mammal in response to a mechanical stimulation of the peripheral sensory nerve of the reference mammal.

15. The system of claim 1, wherein the applying of the biomimetic electrical signal is through multiple channels.

16. The system of claim 15, wherein the signal application module comprises a microelectrode array.

17. The system of claim 1, wherein each of the biomimetic electrical signal, the stimulation reference signal, the stimulated-response signal, and the natural-response signal comprises a spatiotemporal pattern.

18. The system of claim 1, wherein each of the stimulated-response signal and the natural-response signal comprises information regarding at least one of local field potentials, spike times/rates, or spike counts.

19. The system of claim 1, wherein the biomimetic electrical signal is generated from an algorithm based on the stimulation reference signal, the stimulated-response signal, and the natural-response signal.

20. The system of claim 19, wherein the algorithm is derived from a state-space model using the stimulation reference signal, the stimulated-response signal, and the natural-response signal.

21. The system of claim 1, wherein the biomimetic electrical signal is generated by a model predictive controller using a state-space model trained from the stimulation reference signal and the stimulated-response signal and optimized using the natural-response signal.

22. The system of claim 21, wherein the state-space model comprises a discrete-time linear dynamical model trained from the stimulation reference signal and the stimulated-response signal.

23. The system of claim 22, wherein the discrete-time linear dynamical model is defined, at least in part, by equations (1) and (2):

$$x_{t+1} = Ax_t + Bu_t + \epsilon_x \tag{1}$$

$$y_t = Cx_t + \epsilon_y \tag{2}$$

wherein each vector containing stimulation channel magnitudes at time t is denoted $u(t) \in \mathbb{R}^m$, the state is denoted by $x \in \mathbb{R}^n$, and the output is denoted $y \in \mathbb{R}^p$, $\epsilon_x \sim N(0,Q)$ and $\epsilon_y \sim N(0,R)$.

24. The system of claim 23, wherein A, B, C, Q, and R are determined using system identification techniques comprising at least one of subspace identification, least-squares regression with filter bank features as inputs followed by a model reduction technique wherein A, B, and C represent local linearizations of a nonlinear model which include at least one of neural networks, Volterra series models, and kernel regression methods.

25. The system of claim 23, wherein the model predictive controller minimizes a squared Euclidean distance between y(t) and a target output signal.

26. The system of claim 25, wherein the model predictive controller operates to:

minimize $z^T Hz + \kappa \phi(z)$ subject to $Tz = 0$ wherein κ is a weighting parameter to prioritize the contribution of the log barrier, z is formed by stacking the states $x_t$, $u_t$ for t=1, 2, ... length of the control horizon, H represents quadratic penalties imposed by taking Euclidean distances between the output and a desired response signal for each time point, T is the matrix representing the relationships between adjacent time points as in Equation (1).

27. The system of claim 26, wherein:

minimize $z^T Hz + \kappa \phi(z)$ subject to $Tz = 0$ is solved using convex optimization.

28. The system of claim 27, wherein the biomimetic electrical signal is generated by the model predictive controller, optimizing using an average of a plurality of natural-response signals as target waveforms.

29. The system of claim 27, wherein the biomimetic electrical signal is generated by the model predictive controller, optimizing using a target generated from a predictive neural encoding model of a plurality of natural-response signals.

30. The system of claim 27, wherein the model predictive controller employs convex optimization.

31. The system of claim 27, wherein the model predictive controller minimizes mean-square error.

32. The system of claim 1, wherein the activation response comprises a signal emanating from the sensory cortex of the subject mammal.

* * * * *